US008536126B2

(12) United States Patent
Bolt et al.

(10) Patent No.: US 8,536,126 B2
(45) Date of Patent: Sep. 17, 2013

(54) CONJUGATED FACTOR VIII MOLECULES

(71) Applicant: Novo Nordisk A/S, Bagsvaerd (DK)

(72) Inventors: Gert Bolt, Vaerloese (DK); Brian Berg Stidsen Vandahl, Kastrup (DK); Lars Thim, Gentofte (DK); Henning Ralf Stennicke, Kokkedal (DK); Thomas Dock Steenstrup, Gentofte (DK); Shawn DeFrees, North Wales, PA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/759,261

(22) Filed: Feb. 5, 2013

(65) Prior Publication Data

US 2013/0137638 A1    May 30, 2013

Related U.S. Application Data

(63) Continuation of application No. 12/597,473, filed as application No. PCT/US2009/035339 on Feb. 26, 2009.

(60) Provisional application No. 61/032,006, filed on Feb. 27, 2008.

(51) Int. Cl.
*A61K 38/36* (2006.01)
*C07K 14/755* (2006.01)

(52) U.S. Cl.
USPC ........................................................ 514/14.1

(58) Field of Classification Search
None
See application file for complete search history.

(56) References Cited

U.S. PATENT DOCUMENTS

| 4,970,300 A | 11/1990 | Fulton et al. |
|---|---|---|
| 5,298,643 A | 3/1994 | Greenwald |
| 6,048,720 A | 4/2000 | Dalborg et al. |
| 7,199,223 B2 | 4/2007 | Bossard et al. |
| 7,645,860 B2 | 1/2010 | Turecek et al. |
| 7,683,158 B2 | 3/2010 | Siekmann et al. |
| 2006/0115876 A1 | 6/2006 | Pan et al. |
| 2012/0093840 A1* | 4/2012 | Ostergaard et al. ........ 424/178.1 |

FOREIGN PATENT DOCUMENTS

| EP | 1258497 A2 | 11/2002 |
|---|---|---|
| WO | 92/16555 | 10/1992 |
| WO | 03/031464 A2 | 4/2003 |
| WO | 2005/014035 A2 | 2/2005 |
| WO | 2006/103298 A2 | 10/2006 |
| WO | 2007/126808 A1 | 11/2007 |
| WO | 2008/011633 A2 | 1/2008 |
| WO | 2008/025856 A2 | 3/2008 |
| WO | 2008/151258 | 12/2008 |

OTHER PUBLICATIONS

Karin Julenius et al., Glycobiology, "Prediction, Conservation Analysis, and Structural Characterization of Mammalian Mucin-Type O-Glycosylation Sites", 2004, vol. 15, No. 2, pp. 153-164.
P. J. Lenting et al., Haemophilia, "Factor VIII and Von Willebrand Factor—Too Sweet for Their Own Good", 2010, vol. 16, No. 5, pp. 194-199.
Saenko, E. L. et al., Haemophilia, "Strategies Towards a Longer Acting Factor VII", 2006, vol. 12, No. 3, pp. 42-51.
Anne Jessica Fulton, New York University, "Chemical Modification of Human FVIII by Covalent Linkage of Carbohydrate: Preparation of Potential Therapeutic Agent for the Treatment of Hemophilia", 1998, Volume-, Number-, pp. 156.
Fischer et al, PLOS One, "Model for Prediction of Factor VIII Half-Life in Severe Haemophiliacs: Distinct Approaches for Blood Group O and Non-O Patients", 2009, vol. 4, No. 8, pp. e6745.
Hironaka et al, The Journal of Biological Chemistry, "Comparative Studyo F the Sugar Chainosf Factor VI11 Purified from Human Plasma and from the Culture MOEFD RIAE Combinant Baby Hamster Kidney Cells", vol. 267, No. 12, pp. 8012-8020.
Lairson et al, Annual Review of Biochemistry, "Glycosyltransferases: Structures, Functions, and Mechanisms", 2008, vol. 77, Number , pp. 521-555.
Lenting, Blood, "The Life Cycle of Coagulation Factor VIII in View of Its Structure and Function", 1998, vol. 92, Number-, pp. 3983-3996.
Mazsaroff et al, Analytical Chemistry, "Quantitative Comparison of Global Carbohydrate Structures of Glycoproteins Using LC-MS and In-Source Fragmentation", 1997, vol. 69, Number , pp. 2517-2524.
Medzihradszky et al, Analytical Chemistry, "Structural Characteriztaion of Site-Specific N-Glycosylation of Recombinant Human Factor VIII by Reversed-Phase High-Performance Liquid Chromatography-Spectrometry Electrospray Ionization Mass", vol. 69, Number, pp. 3986-3994.
Roberts, M.J et al., Advanced Drug Delivery Reviews, "Chemistry for Peptide and Protein Pegylation", 2002, vol. 54, Number-, pp. 459-476.
Randal J. Kaufman, Thrombosis and Haemostasis, "Post-Translational Modifications Required for Coagulation Factor Secretion and Function", 1998, vol. 79, Number , pp. 1068-1079.
Rostin et al, Bioconjugate Chemistry, "B-Domain Deleted Recombinant Coagulation Factor VIII Modified With Monomethoxy Polyethylene Glycol", 2000, vol. 11, Number , pp. 387-396.
Thim L, et al., Haemophilia, "Purification and Characterization of a New Recombinant Factor VIII(N8)", 2010, vol. 16, No. 2, pp. 349-359.
Vehar, G.A., et al., Nature, "Structure of Human Factor VIII", 1984, vol. 312, Number , pp. 337-342.

\* cited by examiner

*Primary Examiner* — Thomas Heard
(74) *Attorney, Agent, or Firm* — Teresa Chen

(57) ABSTRACT

The present invention relates to B-domain truncated Factor VIII molecules with a modified circulatory half life, said molecule being covalently conjugated with a hydrophilic polymer. The invention furthermore relates to methods for obtaining such molecules as well as use of such molecules.

7 Claims, 9 Drawing Sheets

FIGURE 2
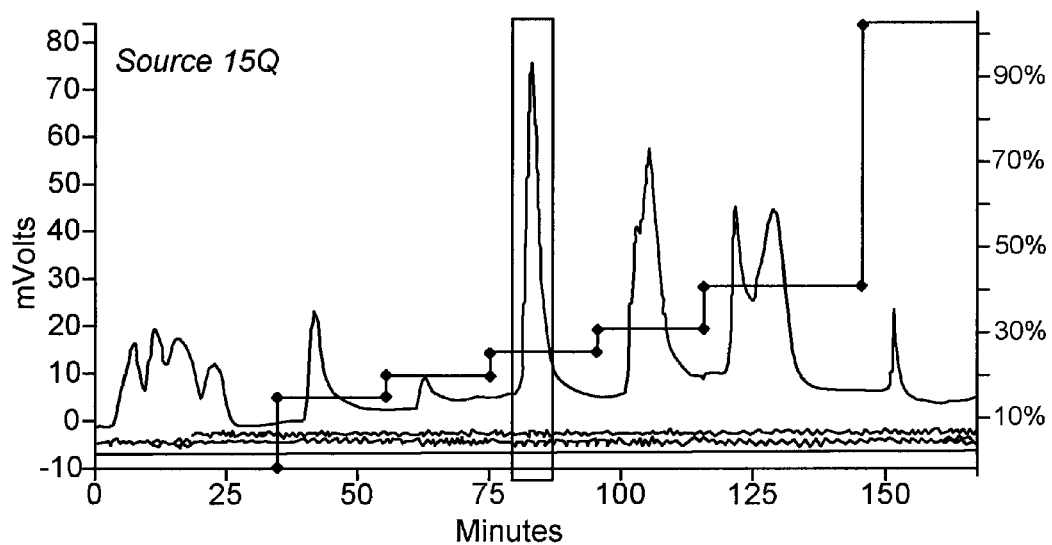
Product Fraction

FIGURE 3
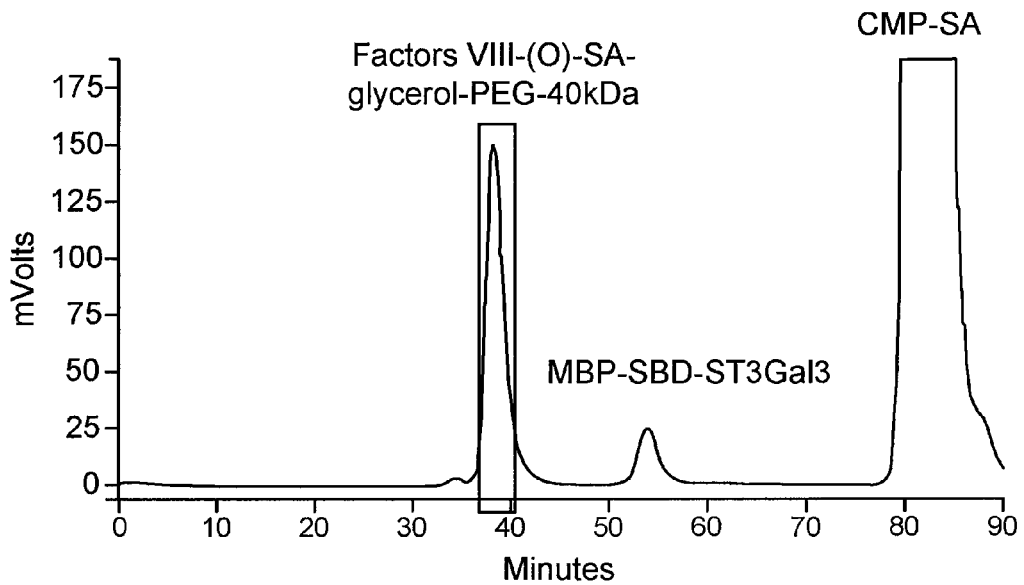
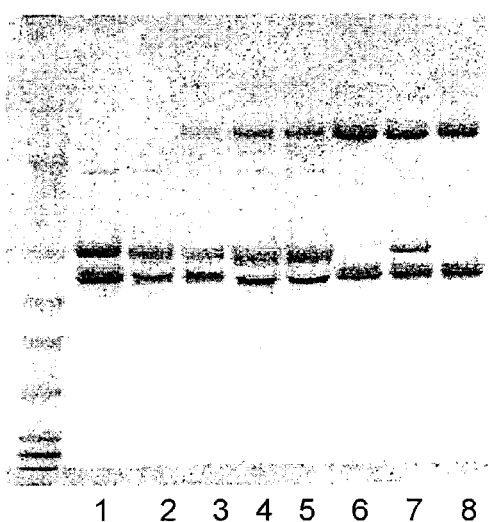
Lane 1; Factor VIII (concentrated)
Lane 2; GlycoPEGylation, 0hrs
Lane 3; GlycoPEGylation, 30hrs
Lane 4; GlycoPEGylatioin, 43hrs
Lane 5; GlycoPEGylation, 49hrs
Lane 6; Source 15Q Product
Lane 7; Capping Reaction (11 hrs)
Lane 8; Superdex 200 Purified Product n > 400 (eg ~ 455); n > 900 (eg ~ 910)

CONJUGATED FACTOR VIII MOLECULES

CROSS REFERENCE TO RELATED APPLICATIONS

This application is a continuation of U.S. patent application Ser. No. 12/597,473, filed Oct. 23, 2009, which is a 35 U.S.C. §371 national stage application of International Patent Application PCT/US2009/035339 (published as WO 2009/108806), filed Feb. 26, 2009; this application further claims priority under 35 U.S.C §119 of U.S. Provisional Application 61/032,006, filed Feb. 27, 2008; the contents of all above-named applications are incorporated herein by reference.

FIELD OF THE INVENTION

The present invention relates to conjugated coagulation Factor VIII molecules. In particular, the present invention relates to conjugated Factor VIII molecules having a modified circulatory half life.

BACKGROUND OF THE INVENTION

Haemophilia A is an inherited bleeding disorder caused by deficiency or dysfunction of coagulation Factor VIII (FVIII) activity. The clinical manifestation is not on primary haemostasis—formation of the blood clot occurs normally—but the clot is unstable due to a lack of secondary thrombin formation. The disease is treated by intravenous injection of coagulation Factor FVIII which is either isolated from blood or produced recombinantly.

Current treatment recommendations are moving from traditional on-demand treatment towards prophylaxis. The circulatory half life of endogenous FVIII is 12-14 hours and prophylactic treatment is thus to be performed several times a week in order to obtain a virtually symptom-free life for the patients. IV administration is for many, especially children and young persons, associated with significant inconvenience and/or pain. There is thus a need in the art for novel Factor VIII products with Factor VIII activity that are preferably homogenous in structure, preferably safe and preferably having a significantly prolonged circulatory half life in order to reduce the number of Factor VIII administration per week. There is furthermore a need in the art for relatively simple methods for obtaining and producing such molecules.

PEGylation of Factor VIII in order to prolong circulatory half life is known in the art. It has however been an obstacle to obtain safe products having a homogenous structure as well as a significantly improved circulatory half life. The available methods of producing conjugated Factor VIII molecules are often laborious, and/or tend to result in low yields and/or products that are not homogenous in structure. The use of artificially engineered O-linked glycosylation sites for obtaining therapeutic proteins having a prolonged circulatory half life of therapeutic proteins has been suggested in WO2008011633, however, no conjugated Factor VIII molecules are disclosed therein.

SUMMARY OF THE INVENTION

In a first aspect, the present invention relates to a B domain truncated Factor VIII molecule with a modified circulatory half life, said molecule being covalently conjugated with a hydrophilic polymer via an O-linked oligosaccharide in the truncated B domain, wherein Factor VIII activation results in removal of the covalently conjugated side group.

In other aspects, the present invention furthermore relates to methods for obtaining such molecules, use of such molecules and pharmaceutical compositions comprising such molecules.

What is thus provided is a conjugated Factor VIII molecule with modified circulatory half life, wherein the conjugated side group (e.g. hydrophilic polymer) is removed upon activation. The molecules according to the invention are preferably homogenous in structure—at least with regard to position of the hydrophilic polymer in the truncated B-domain—and preferably have an advantageous safety profile. Likewise, relatively simple methods for obtaining such molecules are furthermore provided herein. Preferably, activated Factor VIII molecules according to the invention are similar to endogenous activated Factor VIII.

DETAILED DESCRIPTION OF THE INVENTION

Definitions

Factor VIII Molecules:

FVIII/Factor VIII is a large, complex glycoprotein that primarily is produced by hepatocytes. FVIII consists of 2351 amino acids, including signal peptide, and contains several distinct domains, as defined by homology. There are three A-domains, a unique B-domain, and two C-domains. The domain order can be listed as NH2-A1-A2-B-A3-C1-C2-COOH. FVIII circulates in plasma as two chains, separated at the B-A3 border. The chains are connected by bivalent metal ion-bindings. The A1-A2-B chain is termed the heavy chain (HC) while the A3-C1-C2 is termed the light chain (LC).

Endogenous Factor VIII molecules circulate in vivo as a pool of molecules with B domains of various sizes. What probably occurs in vivo is a gradual enzymatic removal of the B domain resulting in a pool of molecules with B-domains of various sizes. It is generally believed that cleavage at position 740, by which the last part of the B-domain is removed, occurs in connection with thrombin activation. However, it cannot be ruled out that a Factor VIII variant in which e.g. the cleavage site at position 740 has been impaired may be active.

"Factor VIII" or "FVIII" as used herein refers to a human plasma glycoprotein that is a member of the intrinsic coagulation pathway and is essential to blood coagulation. "Native FVIII" is the full length human FVIII molecule as shown in SEQ ID NO. 1 (amino acid 1-2332). The B-domain spans amino acids 741-1648 in SEQ ID NO 1.

```
SEQ ID NO 1:
ATRRYYLGAVELSWDYMQSDLGELPVDARFPPRVPKSFPFNTSVVYKKTLFVEFTDHLFNIAKPRPP

WMGLLGPTIQAEVYDTVVITLKNMASHPVSLHAVGVSYWKASEGAEYDDQTSQREKEDDKVFPGGSH

TYVWQVLKENGPMASDPLCLTYSYLSHVDLVKDLNSGLIGALLVCREGSLAKEKTQTLHKFILLFAV

FDEGKSWHSETKNSLMQDRDAASARAWPKMHTVNGYVNRSLPGLIGCHRKSVYWHVIGMGTTPEVHS
```

-continued
```
IFLEGHTFLVRNHRQASLEISPITFLTAQTLLMDLGQFLLFCHISSHQHDGMEAYVKVDSCPEEPQL

RMKNNEEAEDYDDDLTDSEMDVVRFDDDNSPSFIQIRSVAKKHPKTWVHYIAAEEEDWDYAPLVLAP

DDRSYKSQYLNNGPQRIGRKYKKVRFMAYTDETFKTREAIQHESGILGPLLYGEVGDTLLIIFKNQA

SRPYNIYPHGITDVRPLYSRRLPKGVKHLKDFPILPGEIFKYKWTVTVEDGPTKSDPRCLTRYYSSF

VNMERDLASGLIGPLLICYKESVDQRGNQIMSDKRNVILFSVFDENRSWYLTENIQRFLPNPAGVQL

EDPEFQASNIMHSINGYVFDSLQLSVCLHEVAYWYILSIGAQTDFLSVFFSGYTFKHKMVYEDTLTL

FPPFSGETVFMSMENPGLWILGCHNSDFRNRGMTALLKVSSCDKNTGDYYEDSYEDISAYLLSKNNAI

EPRSFSQNSRHPSTRQKQFNATTIPENDIEKTDPWFAHRTPMPKIQNVSSSDLLMLLRQSPTPHGLS

LSDLQEAKYETFSDDPSPGAIDSNNSLSEMTHFRPQLHHSGDMVFTPESGLQLRLNEKLGTTAATEL

KKLDFKVSSTSNNLISTIPSDNLAAGTDNTSSLGPPSMPVHYDSQLDTTLFGKKSSPLTESGGPLSL

SEENNDSKLLESGLMNSQESSWGKNVSSTESGRLFKGKRAHGPALLTKDNALFKVSISLLKTNKTSN

NSATNRKTHIDGPSLLIENSPSVWQNILESDTEFKKVTPLIHDRMLMDKNATALRLNHMSNKTTSSK

NMEMVQQKKEGPIPPDAQNPDMSFFKMLFLPESARWIQRTHGKNSLNSGQGPSPKQLVSLGPEKSVE

GQNFLSEKNKVVVGKGEFTKDVGLKEMVFPSSRNLFLTNLDNLHENNTHNQEKKIQEEIEKKETLIQ

ENVVLPQIHTVTGTKNFMKNLFLLSTRQNVEGSYDGAYAPVLQDFRSLNDSTNRTKKHTAHFSKKGE

EENLEGLGNQTKQIVEKYACTTRISPNTSQQNFVTQRSKRALKQFRLPLEETELEKRIIVDDTSTQW

SKNMKHLTPSTLTQIDYNEKEKGAITQSPLSDCLTRSHSIPQANRSPLPIAKVSSFPSIRPIYLTRV

LFQDNSSHLPAASYRKKDSGVQESSHFLQGAKKNNLSLAILTLEMTGDQREVGSLGTSATNSVTYKK

VENTVLPKPDLPKTSGKVELLPKVHIYQKDLFPTETSNGSPGHLDLVEGSLLQGTEGAIKWNEANRP

GKVPFLRVATESSAKTPSKLLDPLAWDNHYGTQIPKEEWKSQEKSPEKTAFKKKDTILSLNACESNH

AIAAINEGQNKPEIEVTWAKQGRTERLCSQNPPVLKRHQREITRTTLQSDQEEIDYDDTISVEMKKE

DFDIYDEDENQSPRSFQKKTRHYFIAAVERLWDYGMSSSPHVLRNRAQSGSVPQFKKVVFQEFTDGS

FTQPLYRGELNEHLGLLGPYIRAEVEDNIMVTFRNQASRPYSFYSSLISYEEDQRQGAEPRKNFVKP

NETKTYFWKVQHHMAPTKDEFDCKAWAYFSDVDLEKDVHSGLIGPLLVCHTNTLNPAHGRQVTVQEF

ALFFTIFDETKSWYFTENMERNCRAPCNIQMEDPTFKENYRFHAINGYIMDTLPGLVMAQDQRIRWY

LLSMGSNENIHSIHFSGHVFTVRKKEEYKMALYNLYPGVFETVEMLPSKAGIWRVECLIGEHLHAGM

STLFLVYSNKCQTPLGMASGHIRDFQITASGQYGQWAPKLARLHYSGSINAWSTKEPFSWIKVDLLA

PMIIHGIKTQGARQKFSSLYISQFIIMYSLDGKKWQTYRGNSTGTLMVFFGNVDSSGIKHNIFNPPI

IARYIRLHPTHYSIRSTLRMELMGCDLNSCSMPLGMESKAISDAQITASSYFTNMFATWSPSKARLH

LQGRSNAWRPQVNNPKEWLQVDFQKTMKVTGVTTQGVKSLLTSMYVKEFLISSSQDGHQWTLFFQNG

KVKVFQGNQDSFTPVVNSLDPPLLTRYLRIHPQSWVHQIALRMEVLGCEAQDLY
```

The Factor VIII molecules according to the present invention are B domain truncated Factor FVIII molecules wherein the remaining domains correspond to the sequence as set forth in amino acid no 1-740 and 1649-2332 in SEQ ID NO. 1. It follows that molecules according to the invention are recombinant molecules produced in transformed host cells, preferably of mammalian origin. However, the remaining domains (i.e. the three A-domains and the two C-domains) may differ slightly e.g. about 1%, 2%, 3%, 4% or 5% from the amino acid sequence as set forth in SEQ ID NO 1 (amino acids 1-740 and 1649-2332). In particular, it is plausible that amino acid modifications (substitutions, deletions, etc.) are introduced in the remaining domains e.g. in order to modify the binding capacity of Factor VIII with various other components such as e.g. vW factor, LPR, various receptors, other coagulation factors, cell surfaces, etc. Furthermore, it is plausible that the Factor VIII molecules according to the invention comprise other post-translational modifications in e.g. the truncated B-domain and/or in one or more of the other domains of the molecules. These other post-translational modifications may be in the form of various molecules conjugated to the Factor VIII molecule according to the invention such as e.g. polymeric compounds, peptidic compounds, fatty acid derived compounds, etc.

Factor VIII molecules according to the present invention, regardless of whether they are modified outside the B domain or not, have other posttranslational modifications or not, all have Factor VIII activity, meaning the ability to function in the coagulation cascade in a manner functionally similar or equivalent to FVIII, induce the formation of FXa via interaction with FIXa on an activated platelet, and support the formation of a blood clot. The activity can be assessed in vitro by techniques well known in the art such as e.g. clot analysis, endogenous thrombin potential analysis, etc. Factor VIII molecules according to the present invention have FVIII activity being at least about 10%, at least 20%, at least 30%, at least 40%, at least 50%, at least 60%, at least 70%, at least 80%, at least 90%, and 100% or even more than 100% of that of native human FVIII.

B Domain:

The B-domain in Factor VIII spans amino acids 741-1648 in SEQ ID NO 1. The B-domain is cleaved at several different sites, generating large heterogeneity in circulating plasma FVIII molecules. The exact function of the heavily glycosylated B-domain is unknown. What is known is that the domain is dispensable for FVIII activity in the coagulation cascade. This apparent lack of function is supported by the fact that B domain deleted/truncated FVIII appears to have in vivo properties identical to those seen for full length native FVIII. That being said there are indications that the B-domain may reduce the association with the cell membrane, at least under serum free conditions.

B Domain Truncated/Deleted Factor VIII Molecule:

Endogenous full length FVIII is synthesized as a single-chain precursor molecule. Prior to secretion, the precursor is cleaved into the heavy chain and the light chain. Recombinant B domain-deleted FVIII can be produced from two different strategies. Either the heavy chain without the B-domain and the light chain are synthesized individually as two different polypeptide chains (two-chain strategy) or the B-domain deleted FVIII is synthesized as a single precursor polypeptide chain (single-chain strategy) that is cleaved into the heavy and light chains in the same way as the full-length FVIII precursor.

In a B domain-deleted FVIII precursor polypeptide, the heavy and light chain moieties are normally separated by a linker. To minimize the risk of introducing immunogenic epitopes in the B domain-deleted FVIII, the sequence of the linker is preferable derived from the FVIII B-domain. The linker must comprise a recognition site for the protease that separates the B domain-deleted FVIII precursor polypeptide into the heavy and light chain. In the B domain of full length FVIII, amino acid 1644-1648 constitutes this recognition site. The thrombin site leading to removal of the linker on activation of B domain-deleted FVIII is located in the heavy chain. Thus, the size and amino acid sequence of the linker is unlikely to influence its removal from the remaining FVIII molecule by thrombin activation. Deletion of the B domain is an advantage for production of FVIII. Nevertheless, parts of the B domain can be included in the linker without reducing the productivity. The negative effect of the B domain on productivity has not been attributed to any specific size or sequence of the B domain.

The truncated B-domain may contain several O-glycosylation sites. However, according to a preferred embodiment, the molecule comprises only one, alternatively two, three or four O-linked oligosaccharides in the truncated B-domain.

According to a preferred embodiment, the truncated B domain comprises only one potential O-glycosylation site and the hydrophilic polymer is covalently conjugated to this O-glycosylation site.

The O-linked oligosaccharides in the B-domain truncated molecules according to the invention may be attached to O-glycosylation sites that were either artificially created by recombinant means and/or by exposure of "hidden" O-glycosylation sites by truncation of the B-domain. In both cases, such molecules may be made by designing a B-domain truncated Factor VIII amino acid sequence and subsequently subjecting the amino acid sequence to an in silico analysis predicting the probability of O-glycosylation sites in the truncated B-domain. Molecules with a relatively high probability of having such glycosylation sites can be synthesized in a suitable host cell followed by analysis of the glycosylation pattern and subsequent selection of molecules having O-linked glycosylation in the truncated B-domain. Suitable host cells for producing recombinant Factor VIII protein are preferably of mammalian origin in order to ensure that the molecule is glycosylated. In practicing the present invention, the cells are mammalian cells, more preferably an established mammalian cell line, including, without limitation, CHO (e.g., ATCC CCL 61), COS-1 (e.g., ATCC CRL 1650), baby hamster kidney (BHK), and HEK293 (e.g., ATCC CRL 1573; Graham et al., J. Gen. Virol. 36:59-72, 1977) cell lines. A preferred BHK cell line is the tk-ts13 BHK cell line (Waechter and Baserga, Proc. Natl. Acad. Sci. USA 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk-ts13 BHK cell line is also available from the ATCC under accession number CRL 1632. A preferred CHO cell line is the CHO K1 cell line available from ATCC under accession number CC161 as well as cell lines CHO-DXB11 and CHO-DG44.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1); DUKX cells (CHO cell line) (Urlaub and Chasin, Proc. Natl. Acad. Sci. USA 77:4216-4220, 1980) (DUKX cells also being referred to as DXB11 cells), and DG44 (CHO cell line) (Cell, 33: 405, 1983, and Somatic Cell and Molecular Genetics 12: 555, 1986). Also useful are 3T3 cells, Namalwa cells, myelomas and fusions of myelomas with other cells. In some embodiments, the cells may be mutant or recombinant cells, such as, e.g., cells that express a qualitatively or quantitatively different spectrum of enzymes that catalyze post-translational modification of proteins (e.g., glycosylation enzymes such as glycosyl transferases and/or glycosidases, or processing enzymes such as propeptides) than the cell type from which they were derived. DUKX cells (CHO cell line) are especially preferred.

Currently preferred cells are HEK293, COS, Chinese Hamster Ovary (CHO) cells, Baby Hamster Kidney (BHK) and myeloma cells, in particular Chinese Hamster Ovary (CHO) cells.

The inventors of the present invention have thus shown that it is possible to activate "hidden" O-glycosylation sites in the Factor VIII B-domain by truncating the B-domain. While not wishing to be bound by any theory, this phenomenon could be attributable to the tertiary structure of the molecule in the truncated B-domain being altered. "Hidden" O-glycosylation sites are thus "made accessible" to glycosylation in the truncated B-domain. One advantage of this approach is the provision of recombinant molecules with an advantageous safety profile with respect to e.g. allergenicity. Another advantage could be that it may represent a simpler approach of obtaining B-domain truncated variants with an O-linked oligosaccharide in the B-domain due to the inherent abundance of glycosylation sites in the B-domain as it has previously proven difficult to engineer artificial O-glycosylation sites in recombinant proteins.

The length of the B domain in the wt FVIII molecule is about 907 amino acids. The length of the truncated B domain in molecules according to the present invention may vary from about 10 amino acids to about 700 acids, such as e.g. about 12-500 amino acids, 12-400 amino acids, 12-300 amino acids, 12-200 amino acids, 15-100 amino acids, 15-75 amino acids, 15-50 amino acids, 15-45 amino acids, 20-45 amino acids, 20-40 amino acids, or 20-30 amino acids. The truncated B-domain may comprise fragments of the heavy chain and/or the light chain and/or an artificially introduced sequence that is not found in the wt FVIII molecule. The terms "B-domain truncated" and "B-domain deleted" may be used interchangeably herein.

Modified Circulatory Half Life:

Molecules according to the present invention have a modified circulatory half life compared to the wild type Factor VIII molecule, preferably an increased circulatory half life. Circulatory half life is preferably increased at least 10%, preferably at least 15%, preferably at least 20%, preferably at least 25%, preferably at least 30%, preferably at least 35%, preferably at least 40%, preferably at least 45%, preferably at least 50%, preferably at least 55%, preferably at least 60%, preferably at least 65%, preferably at least 70%, preferably at least 75%, preferably at least 80%, preferably at least 85%, preferably at least 90%, preferably at least 95%, preferably at least 100%, more preferably at least 125%, more preferably at least 150%, more preferably at least 175%, more preferably at least 200%, and most preferably at least 250% or 300%. Even more preferably, such molecules have a circulatory half life that is increased at least 400%, 500%, 600%, or even 700% relative to the circulatory half life of the wild type FVIII.

Hydrophilic Polymer:

The modifying group/hydrophilic polymer according to the present invention is preferably non-naturally occurring. In one example, the "non-naturally occurring modifying group" is a polymeric modifying group, in which at least one polymeric moiety is non-naturally occurring. In another example, the non-naturally occurring modifying group is a modified carbohydrate. The locus of functionalization with the modifying group is selected such that it does not prevent the "modified sugar" from being added enzymatically to a polypeptide. "Modified sugar" also refers to any glycosyl mimetic moiety that is functionalized with a modifying group and which is a substrate for a natural or modified enzyme, such as a glycosyltransferase.

The polymeric modifying group added to a polypeptide can alter a property of such polypeptide, for example, its bioavailability, biological activity or its half-life in the body. Exemplary polymers according to the invention include water-soluble polymers that can be linear or branched and can include one or more independently selected polymeric moieties, such as poly(alkylene glycol) and derivatives thereof. The polymeric modifying group according to the invention may include a water-soluble polymer, e.g. poly(ethylene glycol) and derivatives thereof (PEG, m-PEG), poly(propylene glycol) and derivatives thereof (PPG, m-PPG) and the like.

The term "water-soluble" refers to moieties that have some detectable degree of solubility in water. Methods to detect and/or quantify water solubility are well known in the art. Exemplary water-soluble polymers according to the invention include peptides, saccharides, poly(ethers), poly (amines), poly(carboxylic acids) and the like. Peptides can have mixed sequences and be composed of a single amino acid, e.g., poly(lysine). An exemplary polysaccharide is poly (sialic acid). An exemplary poly(ether) is poly(ethylene glycol), e.g., m-PEG. Poly(ethylene imine) is an exemplary polyamine, and poly(acrylic) acid is a representative poly (carboxylic acid).

The polymer backbone of the water-soluble polymer according to the invention can be poly(ethylene glycol) (i.e. PEG). The term PEG in connection with the present invention includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine or cysteine. In one example, the branched poly(ethylene glycol) can be represented in general form as $R(-PEG-OH)_m$ in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

FIG. 8 shows a representative branched PEG polymer of use in embodiments of the invention, referred to herein as "SA-glycerol-PEG." FIG. 8A shows an exemplary SA-glycerol-PEG component of CMP-SA-glycerol-PEG or of a SA-glycerol-PEG linked to a glycan or an amino acid of a polypeptide. FIG. 8B shows the SA-glycerol-PEG moiety linked to a glycan or polypeptide through a Gal residue. FIG. 8C shows the SA-glycerol-PEG moiety linked to a glycan or polypeptide through a Gal-GalNAc residue. FIG. 8D shows the SA-glycerol-PEG moiety linked to an amino acid of a polypeptide through a Gal-GalNAc moiety. In various embodiments, AA is threonine or serine. In an exemplary embodiment, AA is converted to an O-linked glycosylation site by deletion of the B-domain of the FVIII polypeptide. The discussion regarding the molecular weight of the polymer in paragraph hereinbelow under this definition is generally applicable to the branched PEG shown in FIG. 8. In FIG. 8, the index "n" represents any integer providing a linear (and thus a branched) m-PEG of the desired molecular weight. In various embodiments, "n" is selected such that the linear m-PEG moiety is about 20 KDa to about 40 KDa, for example, about 20 KDa, about 30 KDa or about 40 KDa. Integers corresponding to these m-PEG molecular weights correspond to about 400 (e.g. about 455) to about 900 (e.g. about 910). Accordingly, "n" is selected to provide a branched PEG that is about 40 KDa to about 80 KDa, e.g., about 40 KDa, about 50 KDa, about 60 KDa, about 70 KDa, or about 80 KDa.

Many other polymers are also suitable for the invention. Polymer backbones that are non-peptidic and water-soluble, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly ([alpha]-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, as well as copolymers, terpolymers, and mixtures thereof.

Although the molecular weight of each chain of the polymer backbone can vary, it is typically in the range of from about 100 Da to about 160,000 Da, such as e.g., from about 5,000 Da to about 100,000 Da. More specifically, the size of each conjugated hydrophilic polymer according to the present invention may vary from about 500 Da to about 80,000 Da, such as e.g. about 1000 Da to about 80,000 Da; about 2000 Da to about 70,000 Da; about 5000 to about 70,000 Da; about 5000 to about 60,000 Da; about 10,000 to about 70,000 Da; about 20,000 to about 60,000 Da; about 30,000 to about 60,000 Da; about 30,000 to about 50,000 Da; or about 30,000 to about 40,000 Da. It should be understood that these sizes represent estimates rather than exact measures. According to a preferred embodiment, the molecules according to the invention are conjugated with a heterogeneous population of hydrophilic polymers, such as e.g. PEG of a size of e.g. 10,000, 40,000, or 80,000 Da+/− about 5000, about 4000, about 3000, about 2000, or about 1000 Da.

O-Linked Oligosaccharide:

Both N-glycans and O-glycans are attached to proteins by the cells producing the protein. The cellular N-glycosylation machinery recognizes and glycosylates N-glycosylation signals (N—X—S/T motifs) in the amino acid chain, as the nascent protein is translocated from the ribosome to the endoplasmic reticulum (Kiely et al. 1976; Glabe et al. 1980).

Likewise, O-glycans are attached to specific O-glycosylation sites in the amino acid chain, but the motifs triggering O-glycosylation are much more heterogeneous than the N-glycosylation signals, and our ability to predict O-glycosylation sites in amino acid sequences is still inadequate (Julenius et al. 2004). The construction of artificial O-glycosylation sites it is thus associated with some uncertainty. The general assumption is that the native FVIII molecule does not contain any O-glycosylation sites, and the skilled man would therefore expect that at least one artificial O-glycosylation site would have to be constructed and inserted into the B domain in connection with practicing the present invention.

The O-linked oligosaccharide in a truncated Factor VIII B domain may thus be covalently linked to a naturally occurring O-linked glycosylation sequence or an O-linked glycosylation sequence which has been artificially constructed by recombinant techniques.

According to a preferred embodiment of the present invention, the O-linked oligosaccharide is linked to a naturally occurring O-linked glycosylation sequence which is not exposed to glycosylation in the wild type Factor VIII molecule but is becoming accessible to O-glycosylation as a consequence of truncation of the B domain. An example thereof is shown in the examples and in SEQ ID NO 2 (the truncated B-domain corresponds to amino acids 742-763). It is plausible that the "hidden" O-glycosylation site in SEQ ID NO 2 will also become glycosylated even if the B-domain is truncated at a somewhat different place, i.e. if the truncated B domain is somewhat shorter (e.g. 1, 2, 3, 4, or 5 amino acids shorter than SEQ ID NO 2) or longer (such as e.g. 1, 2, 3, 4, 5, 6, 7, 8, 9, 10, 15, 20, 25, 30, 35, 40, 45, or 50 amino acids) compared to SEQ ID NO 2. This approach by activating a "hidden" O-glycosylation site by truncation of a B-domain rather than creation of an artificial O-glycosylation site has the advantage of creating a molecule with an advantageous safety profile (i.e. reduced allergenicity, etc.). Other O-glycosylation sites in the Factor VIII B-domain may likewise become activated by truncating the molecules in different ways.

Glyco-PEGylation of O-Linked Oligosaccharide:

The biosynthesis of O-glycans can be modified and terminated with the addition of sialic acid residues relatively early in biosynthesis. Certain sialyltransferase enzymes are capable of acting on GalNAcα-Ser/Thr, or early O-glycan core subtypes after Core 1 GalT action. The term T antigenis associated with the presence of the Galβ1-3GalNAcα-Ser/Thr disaccharide. Production of these structures involves a competition among glycosyltransferases for the same substrate and thus thue expression levels and subcellular distributions of glycosyltransferases within the Golgi apparatus determines the structural outcome in O-glycan biosynthesis and diversification. As illustrated in FIG. 1, only the Galβ1-3GalNAcα-Ser/Thr disaccharide is amenable for glycoPEGylation.

However, the available amount of this structure may be greatly enhanced through treatment of the protein with sialidase or Corel GalT or a combination thereof. As a result of the glycoPEGylation process the Sialic acid PEG is added to the native structure through an α3 bond to the Galβ1-3GalNAcα-Ser/Thr disaccharide of the target protein (FIG. 1).

Other hydrophilic polymers can also be attached to O-linked oligosaccharides. The basic requirement for enzymatically conjugating other hydrophilic polymers to FVIII via the O-glycan is the ability to couple them to the glycyl-Sialic acid derivative via the free amino group as disclosed in WO03031464. This may be achieved through a large variety of coupling chemistries known to those skilled in the art. Examples of activated biocompatible polymer includes polyalkylene oxides such as without limitation polyethylene glycol (PEG), 2-(methacryloyloxy)ethyl phosphorylcholine (mPC) polymers (as described in WO03062290), dextrans, colominic acids or other carbohydrate based polymers, polymers of amino acids or of specific peptides sequences, biotin derivatives, polyvinyl alcohol (PVA), polycarboxylates, polyvinylpyrrolidone, polyethylene-co-maleic acid anhydride, polystyrene-co-malic acid anhydride, polyoxazoline, poly-acryloylmorpholine, heparin, albumin, celluloses, hydrolysates of chitosan, starches such as hydroxyethyl-starches and hydroxy propyl-starches, glycogen, agaroses and derivatives thereof, guar gum, pullulan, inulin, xanthan gum, carrageenan, pectin, alginic acid hydrolysates, other bio-polymers and any equivalents thereof.

Pharmaceutical Composition:

A pharmaceutical composition is herein preferably meant to encompass compositions comprising Factor VIII molecules according to the present invention suitable for parenteral administration, such as e.g. ready-to-use sterile aqueous compositions or dry sterile compositions that can be reconstituted in e.g. water or an aqueous buffer. The compositions according to the invention may comprise various pharmaceutically acceptable excipients, stabilizers, etc.

Additional ingredients in such compositions may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention. Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the FVIII compound in the form of a nasal or pulmonal spray. As a still further option, the pharmaceutical compositions containing the FVIII compound of the invention may also be adapted to transdermal administration, e.g. by needle-free injection or from a patch, optionally an iontophoretic patch, or transmucosal, e.g. buccal, administration.

In a first aspect the present invention thus relates to a B-domain truncated Factor VIII molecule with a modified circulatory half life, said molecule being covalently conjugated with a hydrophilic polymer via an O-linked oligosaccharide in the truncated B domain, wherein Factor VIII activation (activation of the molecule) results in removal of the covalently conjugated hydrophilic polymer.

According to one embodiment, the hydrophilic polymer is PEG. The size of the PEG polymer may vary from about 10,000 to about 160,000 Da; such as 10,000 to 80,000 Da, such as e.g. about 10,000; 15,000, 20,000; 25,000; 30,000; 35,000; 40,000; 45,000; 50,000; 55,000; 60,000; 65,000, 70,000; 75,000; or 80,000 Da. Preferably, the O-linked oligosaccharide is attached to an O-glycosylation site that is made by truncation of the B-domain and not by inserting an artificial O-glycosylation site that is not found in the wt FVIII molecule.

According to a particularly preferred embodiment, the molecule according to the present invention comprises the amino acid sequence as set forth in SEQ ID NO 2. Such molecules have a unique feature in that the activated FVIII molecule is identical to the native active FVIII molecule. This feature appears to have advantageous properties in safety assessments.

The present invention also relates to pharmaceutical compositions comprising molecules according to the present invention.

The present invention furthermore relates to a method of obtaining a molecule according to the present invention, wherein said method comprises conjugating a B-domain truncated Factor VIII molecule with a hydrophilic polymer, such as e.g. a PEG group, via an O-linked oligosaccharide in the truncated B domain. It follows that the present invention also relates to molecules obtained by or obtainable by such methods.

In another aspect, the present invention relates to a method of treatment of a haemophilic disease comprising administering to a patient in need thereof a therapeutically effective amount of a molecule according to the invention.

The term "treatment", as used herein, refers to the medical therapy of any human or other animal subject in need thereof. Said subject is expected to have undergone physical examination by a medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be prophylactic, palliative, symptomatic and/or curative.

In yet another aspect, the present invention relates to use of a molecule according to the invention as a medicament as well as use of a molecule according to the invention for manufacture of a medicament for treatment of haemophilia.

In a final aspect, the present invention relates to a method of engineering a B-domain truncated Factor VIII molecule according to the present invention, said method comprising (i) truncating the B-domain and optionally subjecting the amino acid sequence of this truncated Factor VIII molecule to an analysis identifying potential O-linked glycosylation sites, (ii) producing the molecule in a suitable host cell and (iii) selecting molecules having O-linked glycans in the truncated B-domain.

BRIEF DESCRIPTION OF THE DRAWINGS

In the figures, the size of the conjugated groups is sometimes referred to as "K", which is herein meant to be equivalent to KDa (kilo Dalton).

FIG. 2: Ion-exchange chromatography of the reaction mixture on Source 15Q (A). SDS-PAGE with molecular markers (left) of collected fraction (B).

FIG. 3: Purification of the capped product on superdex 200 size-exclusion chromatography.

FIG. 8 shows a representative branched PEG polymer of use in embodiments of the invention, referred to herein as "SA-glycerol-PEG. " FIG. 8A shows an exemplary SA-glycerol-PEG component of CMP-SA-glycerol-PEG or of a SA-glycerol-PEG linked to a glycan or an amino acid of a polypeptide. FIG. 8B shows the SA-glycerol-PEG moiety linked to a glycan or polypeptide through a Gal residue. FIG. 8C shows the SA-glycerol-PEG moiety linked to a glycan or polypeptide through a Gal-GalNAc residue. FIG. 8D shows the SA-glycerol-PEG moiety linked to an amino acid of a polypeptide through a Gal-GalNAc moiety.

EXAMPLES

Example 1

Figure 1:
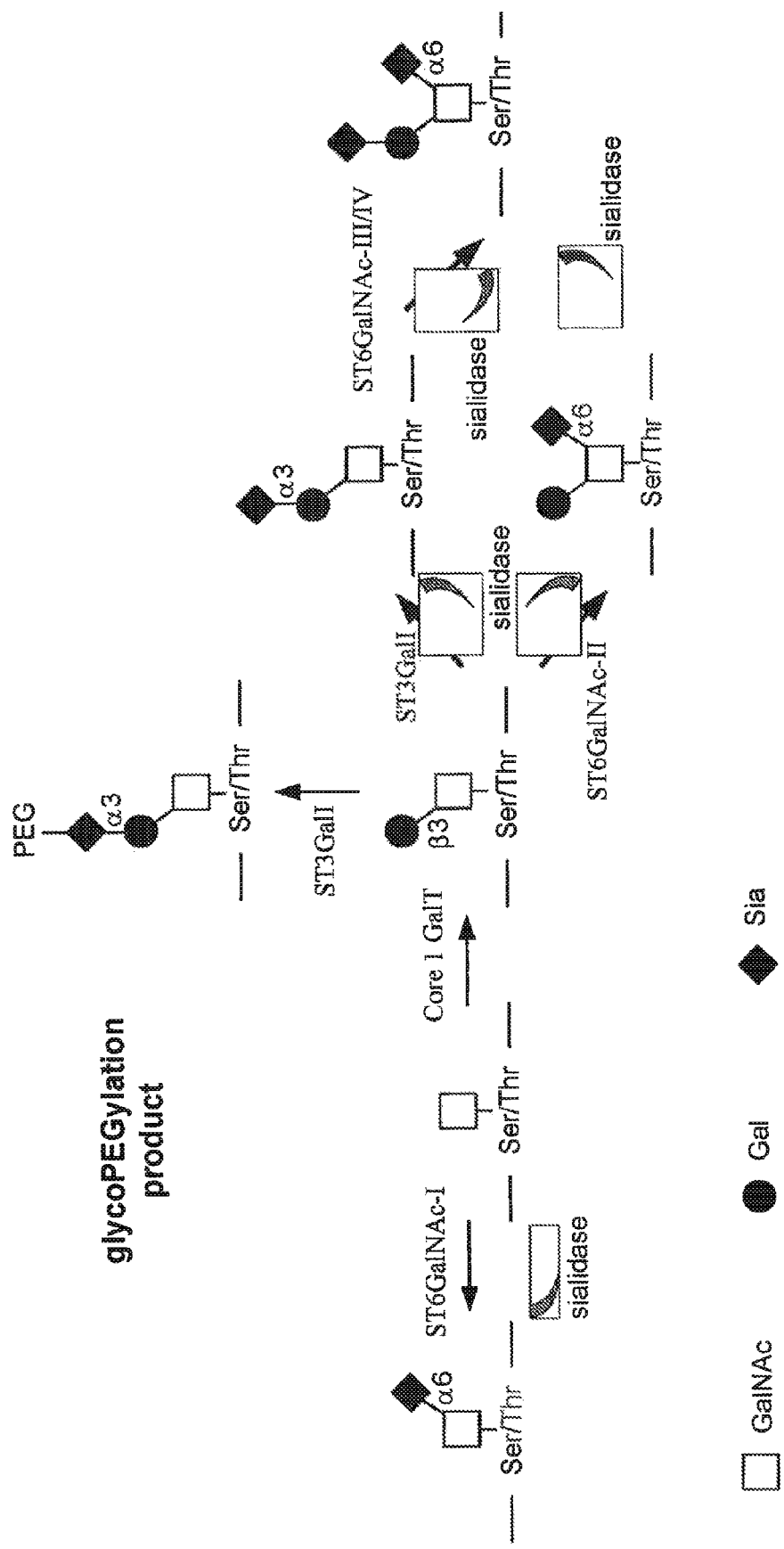
FIG. 1: Schematic drawing of glycol PEGylation process of O-linked oligosaccharides. The figure does not represent an exhaustive list of possible ways to arrive at the products obtained in the examples.

Production of Recombinant B Domain Truncated O-Glycosylated Factor VIII

An example of the amino acid sequence of a B-domain deleted Factor VIII molecule is given in SEQ ID NO 2. This polypeptide may also be referred to as "N8". This molecule comprises a 21 amino acid residue linker sequence (SFSQN-SRHPSQNPPVLKRHQR (SEQ ID NO 3)—the underlined S is the Serine residue with the O-glygan that is pegylated in Example 2).

Factor VIII molecules according to the present invention may in the Examples be referred to in various ways—but all references to Factor VIII molecules refer to Factor VIII molecules according to the invention, or alternatively Factor VIII molecules in the process of being converted to Factor VIII molecules according to the invention.

SEQ ID NO 2:
ATRRYYLGAVELSWDYMQSDLGELPVDARFPPRVPKSFPFNTSVVYKKTLFVEFTDHLFNIAKPRP

PWMGLLGPTIQAEVYDTVVITLKNMASHPVSLHAVGVSYWKASEGAEYDDQTSQREKEDDKVFPGG

```
-continued
SHTYVWQVLKENGPMASDPLCLTYSYLSHVDLVKDLNSGLIGALLVCREGSLAKEKTQTLHKFILL

FAVFDEGKSWHSETKNSLMQDRDAASARAWPKMHTVNGYVNRSLPGLIGCHRKSVYWHVIGMGTTP

EVHSIFLEGHTFLVRNHRQASLEISPITFLTAQTLLMDLGQFLLFCHISSHQHDGMEAYVKVDSCP

EEPQLRMKNNEEAEDYDDDLTDSEMDVVRFDDDNSPSFIQIRSVAKKHPKTWVHYIAAEEEDWDYA

PLVLAPDDRSYKSQYLNNGPQRIGRKYKKVRFMAYTDETFKTREAIQHESGILGPLLYGEVGDTLL

IIFKNQASRPYNIYPHGITDVRPLYSRRLPKGVKHLKDFPILPGEIFKYKWTVTVEDGPTKSDPRC

LTRYYSSFVNMERDLASGLIGPLLICYKESVDQRGNQIMSDKRNVILFSVFDENRSWYLTENIQRF

LPNPAGVQLEDPEFQASNIMHSINGYVFDSLQLSVCLHEVAYWYILSIGAQTDFLSVFFSGYTFKH

KMVYEDTLTLFPFSGETVFMSMENPGLWILGCHNSDFRNRGMTALLKVSSCDKNTGDYYEDSYEDI

SAYLLSKNNAIEPRSFSQNSRHPSQNPPVLKRHQREITRTTLQSDQEEIDYDDTISVEMKKEDFDI

YDEDENQSPRSFQKKTRHYFIAAVERLWDYGMSSSPHVLRNRAQSGSVPQFKKVVFQEFTDGSFTQ

PLYRGELNEHLGLLGPYIRAEVEDNIMVTFRNQASRPYSFYSSLISYEEDQRQGAEPRKNFVKPNE

TKTYFWKVQHHMAPTKDEFDCKAWAYFSDVDLEKDVHSGLIGPLLVCHTNTLNPAHGRQVTVQEFA

LFFTIFDETKSWYFTENMERNCRAPCNIQMEDPTFKENYRFHAINGYIMDTLPGLVMAQDQRIRWY

LLSMGSNENIHSIHFSGHVFTVRKKEEYKMALYNLYPGVFETVEMLPSKAGIWRVECLIGEHLHAG

MSTLFLVYSNKCQTPLGMASGHIRDFQITASGQYGQWAPKLARLHYSGSINAWSTKEPFSWIKVDL

LAPMIIHGIKTQGARQKFSSLYISQFIIMYSLDGKKWQTYRGNSTGTLMVFFGNVDSSGIKHNIFN

PPIIARYIRLHPTHYSIRSTLRMELMGCDLNSCSMPLGMESKAISDAQITASSYFTNMFATWSPSK

ARLHLQGRSNAWRPQVNNPKEWLQVDFQKTMKVTGVTTQGVKSLLTSMYVKEFLISSSQDGHQWTL

FFQNGKVKVFQGNQDSFTPVVNSLDPPLLTRYLRIHPQSWVHQIALRMEVLGCEAQDLY
```

Cell Line and Culture Process:

Using Factor VIII cDNA a mammalian expression plasmid encoding B-domain deleted Factor VIII having an amino acid sequence as set forth in SEQ ID NO 2 was constructed. The plasmid is encoding Factor VIII heavy chain comprising amino acid 1-740 of full length human Factor VIII and Factor VIII light chain comprising amino acid 1649-2332 of full length human Factor VIII. The heavy and light chain sequences are connected by a 21 amino acid linker with the sequence of amino acid 741-750 and 1638-1648 of full length human Factor VIII. Chinese hamster ovary (CHO) cells were transfected with the BDD Factor VIII coding plasmid and selected with the dihydrofolate reductase system eventually leading to a clonal suspension producer cell cultivated in animal component-free medium.

The first step in the process is the inoculation of a cell vial, from a working cell bank vial, into a chemically defined and animal component free growth medium. Initially after thawing, the cells are incubated in a T-flask. One or two days after thawing, the cells are transferred to a shaker flask, and the culture volume is expanded by successive dilutions in order to keep the cell density between $0.2$-$3.0 \times 10^6$ cells/ml. The next step is the transfer of the shaker flask culture into seed bioreactors. The culture volume is here further expanded before the final transfer to the production bioreactor. The same chemically defined and animal component free medium is used for all the inoculum expansion steps. After transfer to the production bioreactor, the medium is supplemented with components that increase the product concentration. In the production bioreactor the cells are cultured in a repeated batch process with a cycle time of three days. At harvest, 80-90% of the culture volume is transferred to a harvest tank. The remaining culture fluid is then diluted with fresh medium, in order to obtain the initial cell density, and then a new growth period is initiated.

The harvest batch is clarified by centrifugation and filtration and transferred to a holding tank before initiation of the purification process. A buffer is added to the cell free harvest in the holding tank to stabilise pH.

By the end of the production run, cells are collected and frozen down, in order to make an end of production cell bank. This cell bank is tested for mycoplasma, sterility and viral contamination.

Purification:

For the isolation of B-domain-deleted Factor VIII from cell culture media, a four step purification procedure was used including a concentration step on a Capto MMC column, an immunoabsorbent chromatography step, an anionic exchange chromatography and finally a gelfiltration step. Typically the following procedure was used: 11 litre of sterile filtered medium was pumped onto at column (1.6×12 cm) of Capto MMC (GE Healthcare, Sweden) equilibrated in buffer A: 20 mM imidazole, 10 mM $CaCl_2$, 50 mM NaCl, 0.02% Tween 80, pH=7.5 at a flow of 15 ml/min. The column was washed with 75 ml of buffer A followed by wash with 75 ml of buffer A containing 1.5 M NaCl. The protein was eluted with 20 mM imidazole, 10 mM $CaCl_2$, 0.02% Tween 80, 2.5 M NaCl, 8 Methyleneglycol, pH=7.5 at a flow of 1 ml/min. Fractions of 8 ml were collected and assayed for Factor VIII activity (CoA-test). Factor VIII containing fractions were pooled and normally a pool volume of around 50 ml was obtained.

A monoclonal antibody against Factor VIII has been developed (Kjalke Eur J Biochem 234 773). By epitope mapping (results not shown) this antibody, F25, was found to recognise the far C-terminal sequence of the heavy chain from amino acid residue 725 to 740. The F25 antibody was coupled to NHS-activated Sepharose 4 FF (GE Healthcare, Bio-Sciences AB, Uppsala, Sweden) at a density of 2.4 mg per ml of gel essentially as described by the manufacturer. The pool from the previous step was diluted 10 times with 20 mM imidazole, 10 mM $CaCl_2$, 0.02% Tween 80, pH=7.3 and applied to the F25 Sepharose column (1.6×9.5 cm) equilibrated with 20 mM imidazole, 10 mM $CaCl_2$, 150 mM NaCl, 0.02% Tween 80, 1 M glycerol pH=7.3 at a flow of 0.5 ml/min. The column was washed with equilibration buffer until the UV signal was constant and then with 20 mM imidazole, 10 mM $CaCl_2$, 0.65 M NaCl, pH=7.3 until the UV signal was constant again. Factor VIII was eluted with 20 mM imidazole, 10 mM $CaCl_2$, 0.02% Tween 80, 2.5 M NaCl, 50% ethyleneglycol, pH=7.3 at a flow of 1 ml/min. Fractions of 1 ml were collected and assayed for Factor VIII activity (CoA-test). Factor VIII containing fractions were pooled and normally a pool volume of around 25 ml was obtained.

A buffer A: 20 mM imidazole, 10 mM $CaCl_2$, 0.02% Tween 80, 1 M glycerol, pH=7.3 and a buffer B: 20 mM imidazole, 10 mM $CaCl_2$, 0.02% Tween 80, 1 M glycerol, 1 M NaCl, pH=7.3 was prepared for the ion-exchange step. A column (1×10 cm) of Macro-Prep 25Q Support (Bio-Rad Laboratories, Hercules, Calif., USA) was equilibrated with 85% buffer A/15% Buffer B at a flow of 2 ml/min. The pool from the previous step was diluted 10 times with buffer A and pumped onto the column with a flow of 2 ml/min. The column was washed with 85% buffer A/15% buffer B at a flow of 2 ml/min and Factor VIII was eluted with a linear gradient from 15% buffer B to 70% buffer B over 120 ml at a flow of 2 ml/min. Fractions of 2 ml were collected and assayed for Factor VIII activity (CoA-test). Factor VIII containing fractions were pooled and normally a pool volume of around 36 ml was obtained.

The pool from the previous step was applied to a Superdex 200, prep grade (GE Healthcare, Bio-Sciences AB, Uppsala, Sweden) column (2.6×60 cm) equilibrated and eluted at 1 ml/min with 20 mM imidazole, 10 mM $CaCl_2$, 0.02% Tween 80, 1 M glycerol, 150 mM NaCl, pH=7.3. Fractions of 3 ml were collected and assayed for Factor VIII activity (CoA-test). Factor VIII containing fractions were pooled and normally a pool volume of around 57 ml was obtained. The pool containing Factor VIII was store at −80° C.

With the use of the above four-step purification procedure an overall yield of approximately 15% was obtained as judged by CoA activity and ELISA measurements.

The cell line used for manufacture of N8 is a recombinant Chinese hamster ovary (CHO) cell line stably transfected with expression plasmid #814 F8-500 in pTSV7 consisting of the pTSV7 expression vector with an insert containing cDNA encoding the F8-500 protein. "N8" is herein meant to correspond to a protein having an amino acid sequence as listed in SEQ ID NO 2. Starting at the N-terminus, the F8-500 protein (N8) consists of the FVIII signal peptide (amino acids-19 to -1) followed by the FVIII heavy chain without the B domain (amino acids 1-740), a 21 amino acid linker (SFSQN-SRHPSQNPPVLKRHQR), and the FVIII light chain (amino acids 1649-2332 of wild-type human FVIII). The sequence of the 21 amino acid linker is derived from the FVIII B domain and consists of amino acids 741-750 and 1638-1648 of full length FVIII.

CHO cells were transfected with 814 F8-500 in pTSV7 and selected with the dihydrofolate reductase system eventually leading to a clonal suspension producer cell cultivated in animal component-free medium. A production run is initiated by thawing a working cell bank vial and expanding the cells until transfer to a production bioreactor. The same chemically defined and animal component free medium is used for all the inoculum expansion steps. After transfer to the production bioreactor, the medium is supplemented with components that increase the product concentration. In the production bioreactor the cells are cultured in a repeated batch process with a cycle time of three days. At harvest, 80-90% of the culture volume is transferred to a harvest tank. The remaining culture fluid is then diluted with fresh medium, in order to obtain the initial cell density, and then a new growth period is initiated. The harvest batch is clarified by centrifugation and filtration and transferred to a holding tank before initiation of the purification process. A buffer is added to the cell free harvest in the holding tank to stabilize pH.

Example 2

PEGylation of Recombinant B Domain Truncated and O-Glycosylated Factor VIII

The recombinant Factor VIII molecules obtained in Example 1 are conjugated with polyethylenglycol (PEG) using the following procedure:

For the glycoPEGylation of the recombinant Factor VIII molecules obtained in Example 1 to be efficient a FVIII concentration >5 mg/ml is preferred. Since FVIII is not normally soluble at the concentration a screening of selected buffer compositions was conducted (see some of these results in table 1).

Based on these considerations, a buffer containing 50 mM MES, 50 mM $CaCl_2$, 150 mM NaCl, 20% glycerol, pH 6.0 was found to be a suitable reaction buffer.

TABLE 1

Evaluation of impact of reaction conditions on FVIII solubility and aggregation.

| Reaction buffer composition | Precipitate | % Aggregate |
|---|---|---|
| 10 mM Histidine, 260 mM Glycine, 1% Sucrose, 10 mM CaCl2 | YES | n.d. |
| 50 mM HEPES, 10 mM CaCl2, 150 mM NaCl, pH 7; | YES | n.d. |
| 50 mM MES, 10 mM CaCl2, 150 mM NaCl, pH 6.0 | YES | n.d. |
| 50 mM MES, 50 mM CaCl2, 150 mM NaCl, pH 6.0 | NO | 8 |
| 50 mM MES, 50 mM CaCl2, 150 mM NaCl, 10% glycerol, pH 6.0 | NO | 5 |
| 50 mM MES, 50 mM CaCl2, 150 mM NaCl, 20% glycerol, pH 6.0 | NO | 1.0-1.7 |

Recombinant FVIII which had been purified as described above was concentrated in reaction buffer either by ion exchange on a Poros 50 HQ column using step elution, on a Sartorius Vivaspin (PES) filter, 10 kDa cut-off or on an Amicon 10 kDa MWCO PES filter to a concentration of 6-10 mg/mL. The glycoPEGylation of FVIII was initiated by mixing Factor VIII (BDD) (~4.7 mg/mL final) with Sialidase (A. urifaciens) (159 mU/mL), CMP-SA-glycerol-PEG-40 kDa (5 mol.eq.) and MBP-ST3Gal1 (540 mU) in reaction buffer (50 mM MES, 50 mM CaCl2, 150 mM NaCl, 20% glycerol, 0.5 mM antipain, pH 6.0). The reaction mixture was incubated at 32° C. until a conversion yield of ~20-30% of total.

Following the incubation the sample was diluted with Buffer A (25 mM Tris, 5 mM CaCl$_2$, 20 mM NaCl, 20% glycerol, pH 7.5) and applied onto a Source 15Q column (1 cm id×6 cm, 4.7 mL, 1 mL/min, 280 nm). The bound material was washed with Buffer A and eluted using a step gradient with Buffer B (25 mM Tris, 5 mM CaCl$_2$, 1 M NaCl, 20% glycerol, pH 7.5). GlycoPEGylated Factor VIII-(O)-SA-glycerol-PEG-40 kDa was eluted from the column at ~25% Buffer B. FIG. 2 shows ion-exchange chromatography of the reaction mixture on Source 15Q.

In order to block free galactose moieties which had been exposed on the N-glycans during the sialidase treatment the pooled fraction of Factor VIII-SA-glycerol-PEG-40 kDa (1.0 mg/mL final) was mixed with CMP-SA (2,000 mol eq) and MBP-SBD-ST3Gal3 (400 mU/mL) in reaction buffer 50 mM MES, 20 mM CaCl2, 150 mM NaCl, 10 mM MnCl2, 20% glycerol, pH 6.0 and incubated at 32° C. for 11 hours.

The resulting capped, glycoPEGylated Factor VIII-SA-glycerol-PEG-40 kDa was seperated from CMP-SA and ST3GalIII by gel-filtration on a Superdex 200 column (10 cm id×300 mm; 280 nm) equilibrated with 50 mM MES, 50 mM CaCl$_2$, 150 mM NaCl, 10% glycerol, pH 6.0; flow rate of 0.25 mL/min. The product Factor VIII-SA-glycerol-PEG-40 kDa elutes at 38 min. FIG. 3 shows purification of the capped product using Superdex 200 size-exclusion chromatography. The peak fraction was collected, aliquoted and subjected to subsequent analysis.

The purpose of the capping procedure is to reduce in vivo clearance of the conjugated Factor VIII molecule.

Example 3

Activity of O-Glycan PEGylated rFVIII in Chromogenic FVIII Activity Assay

The activity of the O-glycoPEGylated rFVIII obtained in Example 2 was evaluated in a chromogenic FVIII assay using Coatest SP reagents (Chromogenix) as follows: rFVIII samples and calibrator (the 7th international FVIII standard from NIBSC) were diluted in Coatest assay buffer (50 mM Tris, 150 mM NaCl, 1% BSA, pH 7.3, with preservative). Fifty nl of samples, standards, and buffer negative control were added to 96-well microtiter plates (Nunc) in duplicates. The Factor IXa/Factor X reagent, the phospholipid reagent and CaCl$_2$ from the Coatest SP kit were mixed 5:1:3 (vol:vol:vol) and 75 µl of this added to the wells. After 15 min incubation at room temperature 50 µl of the Factor Xa substrate S-2765/thrombin inhibitor I-2581 mix was added and the reactions incubated 10 min at room temperature before 25 µl 1 M citric acid, pH 3, was added. The absorbance at 415 nm was measured on a Spectramax microtiter plate reader (Molecular Devices) with absorbance at 620 nm used as reference wavelength. The value for the negative control was subtracted from all samples and a calibration curve prepared by linear regression of the absorbance values plotted vs. FVIII concentration. The specific activity was calculated by dividing the activity of the samples with the protein concentration determined by size exclusion HPLC by integrating the light chain peak in the HPLC chromatogram, i.e. the PEG-moiety was not included. The data in table 2 demonstrate that the specific chromogenic activity was maintained for the O-glycoPEGylated rFVIII compounds, meaning that Factor VIII activity appear to be retained in the PEGylated variants.

TABLE 2

Specific chromogenic activity of O-glycoPEGylated rFVIII with different PEG group sizes.

| rFVIII compound | Specific chromogenic activity (IU/mg) |
|---|---|
| rFVIII | 11819 ± 727 (5) |
| 10KDa-PEG-[O]-rFVIII | Approx 8331 (1) |
| 40KDa-PEG-[O]-rFVIII | 9760 ± 886 (8) |
| 80KDa-PEG-[O]-rFVIII | 12129 ± 2643 (3) |

Data are mean and standard deviations of the numbers of independent determinations noted in parentheses Example 4

Activity of O-Glycan PEGylated rFVIII in FVIII Clotting Activity Assay

The activity of the O-glycoPEGylated rFVIII was further evaluated in FVIII clotting assay. rFVIII samples were diluted in HBS/BSA (20 mM hepes, 150 mM NaCl, pH 7.4 with 1% BSA) to approximately 10 U/ml followed by 10-fold dilution in FVIII-deficient plasma containing VWF (Dade Behring). The samples and a calibrated plasma standard (HemosIL Calibration Plasma from Instrumentation Laboratory) were subsequently diluted in HBS/BSA to four (samples) or six (calibrator) different concentrations. The clotting time was measured on an ACL9000 instrument (Instrumentation laboratory) using the single factor program, where samples/standards were mixed with equal volumes of FVIII-deficient plasma with VWF (Dade Behring), calcium and aPTT reagents, and the clotting time measured. As reagents the following were used: Synthasil (HemosIL, Instrumentation Laboratory), Actin FS (Activated PTT Reagent, Dade Behring) Stago (STA® PTT-A, Stago), and dAPPTin (DAPPTIN®TC, Technoclone). The activities of the samples were calculated based on a semi-log plot of clotting time versus concentration of the calibrator.

The clotting activity (FIG. 4) of the O-glycoPEGyated rFVIII compounds (control, 10, 40, and 80 kDA PEG, respectively) was decreased to various extend depending on the PEG size and the aPTT reagents used. Using Synthasil or dAPPTin as aPTT reagents resulted in a gradual decrease in clotting activity with PEG-size. With Stago's aPTT reagent, a 50% lower specific clotting activity was observed for all three O-glycoPEGylated N8 compounds evaluated. When Actin FS was used as aPTT reagent a specific clotting activity around 10,000 IU/mg was maintained. The data indicates that the aPTT assay is influenced by the presence of a PEG moiety, however, using a selected aPTT reagents e.g. Actin FS the specific clotting activity of rFVIII is not impaired upon O-glycoPEGylation.

Example 5

Effect of O-Linked PEGylation of rFVIII on Co-Factor Activity and Rate of FVIII Activation Incorporation of activated FVIII into the FIXa-FVIIIa complex enhances the catalytic efficiency of FIXa-catalyzed FX activation five orders of magnitude (van Dieij en et al. (1981) *J Biol Chem* 256:3433) and characterization of FIXa-FVIIIa complex assembly and FX activation kinetics is a sensitive measure of the functional integrity of FVIIIa molecules. The co-factor activity of thrombin-activated rFVIII or PEG-rFVIII was characterized by determining the kinetic parameters of FIXa-catalyzed FX activation in the presence of phospholipids and thrombin-activated rFVIII or PEG-rFVIII. Using the FVIIIa activity assay (FIXa-cofactor activity assay), reciprocal titrations of FIXa and FVIIIa against a fixed concentration (0.1 nM) of rFVIIIa or FIXa, respectively, were performed to obtain apparent affinity of FIXa for rFVIIIa ($K_{1/2FIXa}$) and functional FVIIIa concentration. The Michaelis constant ($k_m$) and turn-over number ($k_{cat}$) of FX activation were obtained from titrations of FX against a fixed concentration of FIXa-FVIIIa complex.

The FIXa-cofactor activity assays was carried out as follows: Thrombin-activated rFVIII and PEG-rFVIII variants were prepared freshly for each test by incubating rFVIII (usually 0.7 nM, 1 U/mL) with 5 nM human α-thrombin for exactly 30 seconds at 37° C. Subsequently, the rate of FX activation was quantified by subsampling the activation reaction above into a prepared mixture of FIXa, phospholipid vesicles (Phospholipid TGT from Rossix [Mölndal, Sweden]), hirudin, Pefabloc Xa and $CaCl_2$; FX activation was initiated by addition of FX and allowed to proceed for either 30 seconds or 60 seconds at 37° C. Activation was stopped by dilution of the FX activation reaction into ice cold buffer containing EDTA. Using a FXa specific chromogenic substrate, the concentration of FXa was quantified by reading absorbance at 405 nM in an ELISA reader. A reference curve prepared using purified FXa was used to convert absorbance to FXa concentration. The turn-over number of FIXa-rFVIIIa complexes assembled from activated rFVIII or PEG-rFVIII variants was used to convert the rate of FX activation to rFVIIIa concentration.

The rate of thrombin-catalyzed rFVIII activation was measured by quantifying the initial (0 to 3 min) formation of rFVIIIa in a mixture containing 0.7 nM rFVIII or PEG-rFVIII and 0.13 nM human α-thrombin. Formation of FVIIIa was linear in time. The rate of FVIIIa activation was expressed as moles rFVIIIa formed per minute per mole of rFVIII initially present ($v/[rFVIII]_0$).

O-linked glycoPEGylation of rFVIII did not affect the rate of thrombin-catalyzed rFVIII activation or the $k_m$ or $k_{cat}$ of FIXa-catalyzed activation of FX in the presence of activated rFVIII (see Table 3). Furthermore, O-linked glycoPEGylation did not affect the apparent $K_d$ of rFVIIIa-FIXa interaction ($K_{1/2FIXa}$).

Figure 4A:
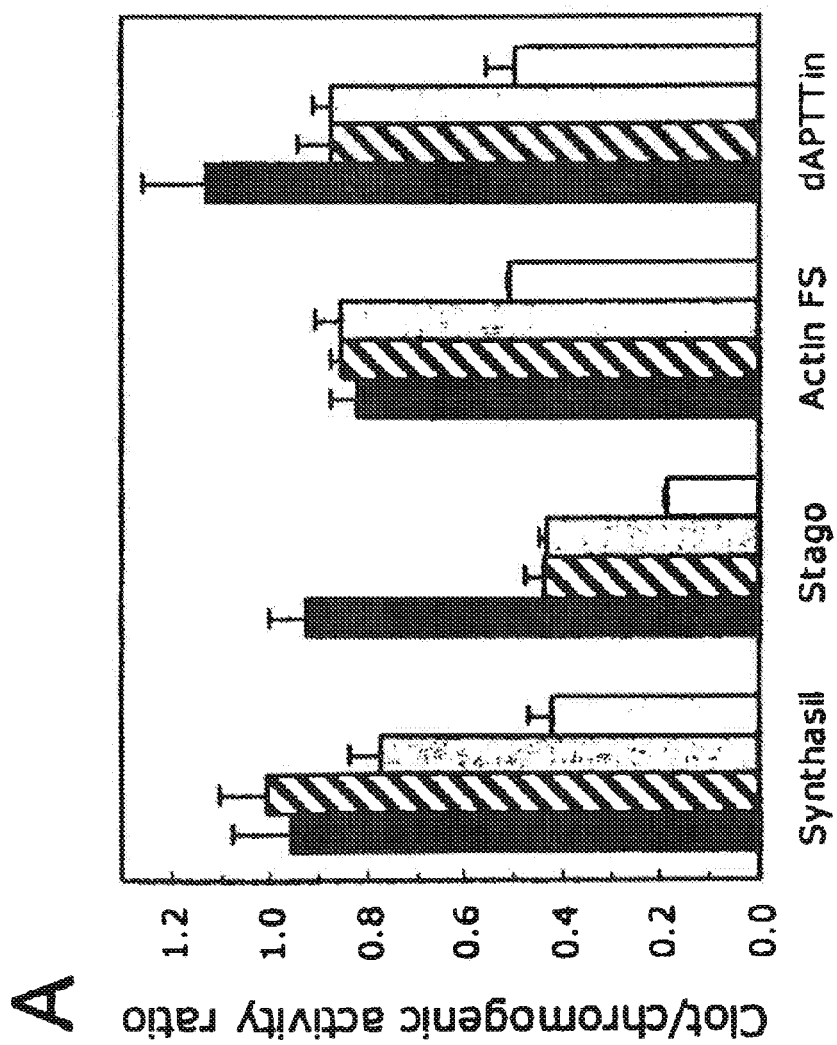
FIG. 4: Clotting activity of O-glycoPEGylated rFVIII using various aPTT reagents. (A) shows the ration between the clotting activity and the chromogenic activity. (B) shows the specific clotting activity.
Figure 4B:
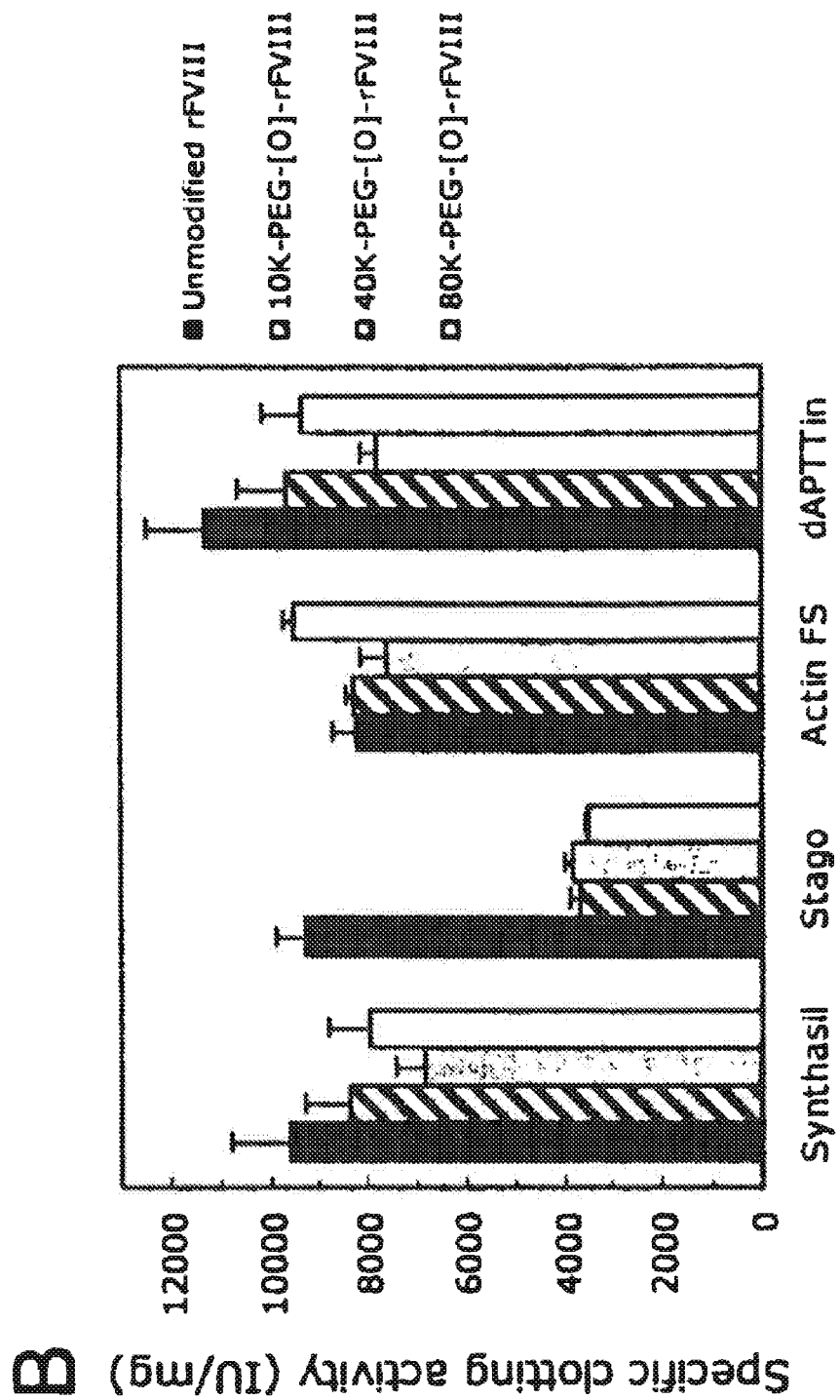
Figure 5:
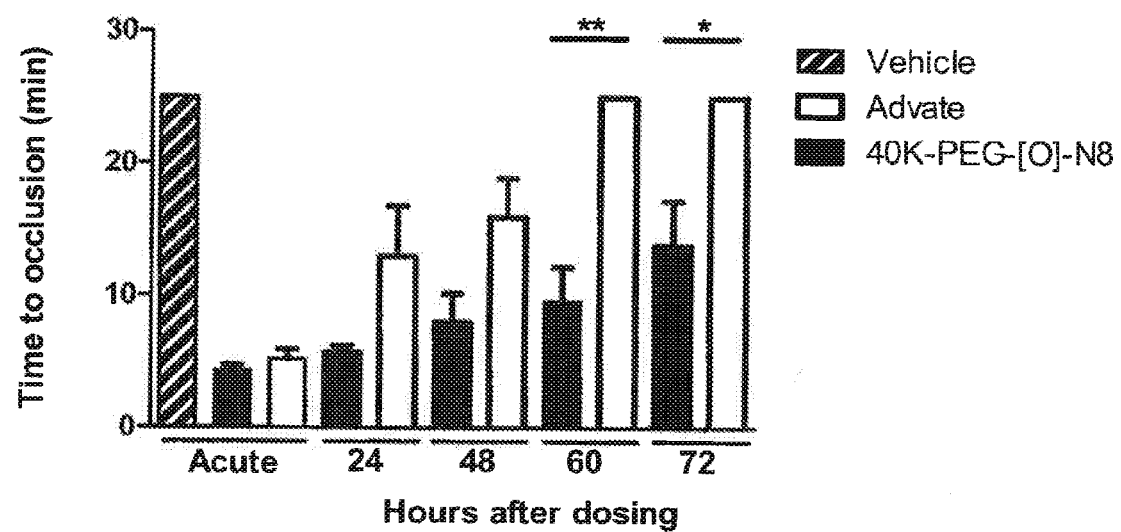
FIG. 5: In vivo effects (time to occlusion) in FVIII KO mice of 40K-PEG-[O]-N8
Figure 6:
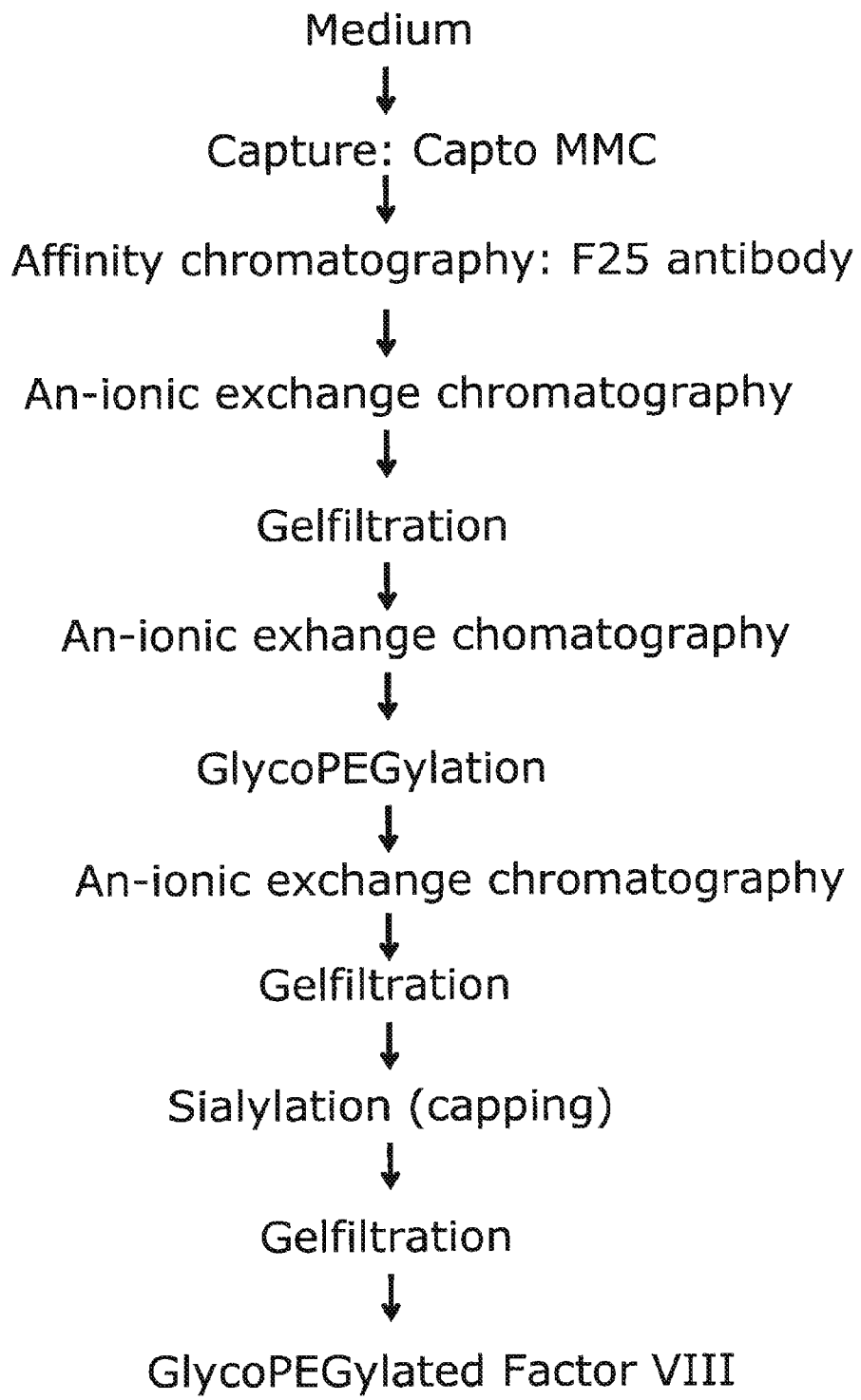
FIG. 6: Flow diagram showing the process steps involved in production of glycoPEGylated Factor FVIII according to the invention.
Figure 7:
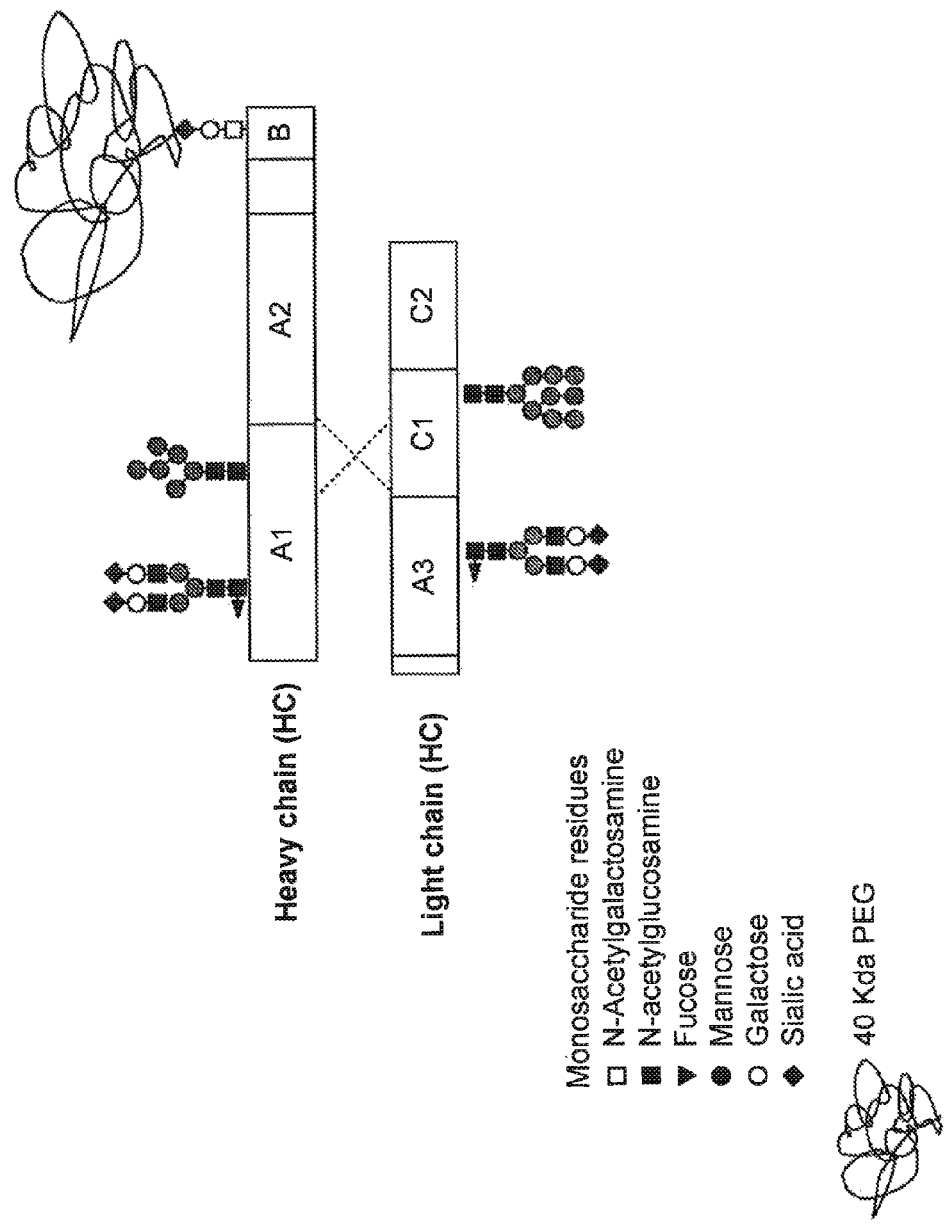
FIG. 7: Schematic representation of a Factor VIII molecule according to the present invention produced in the Examples.
Figure 8:
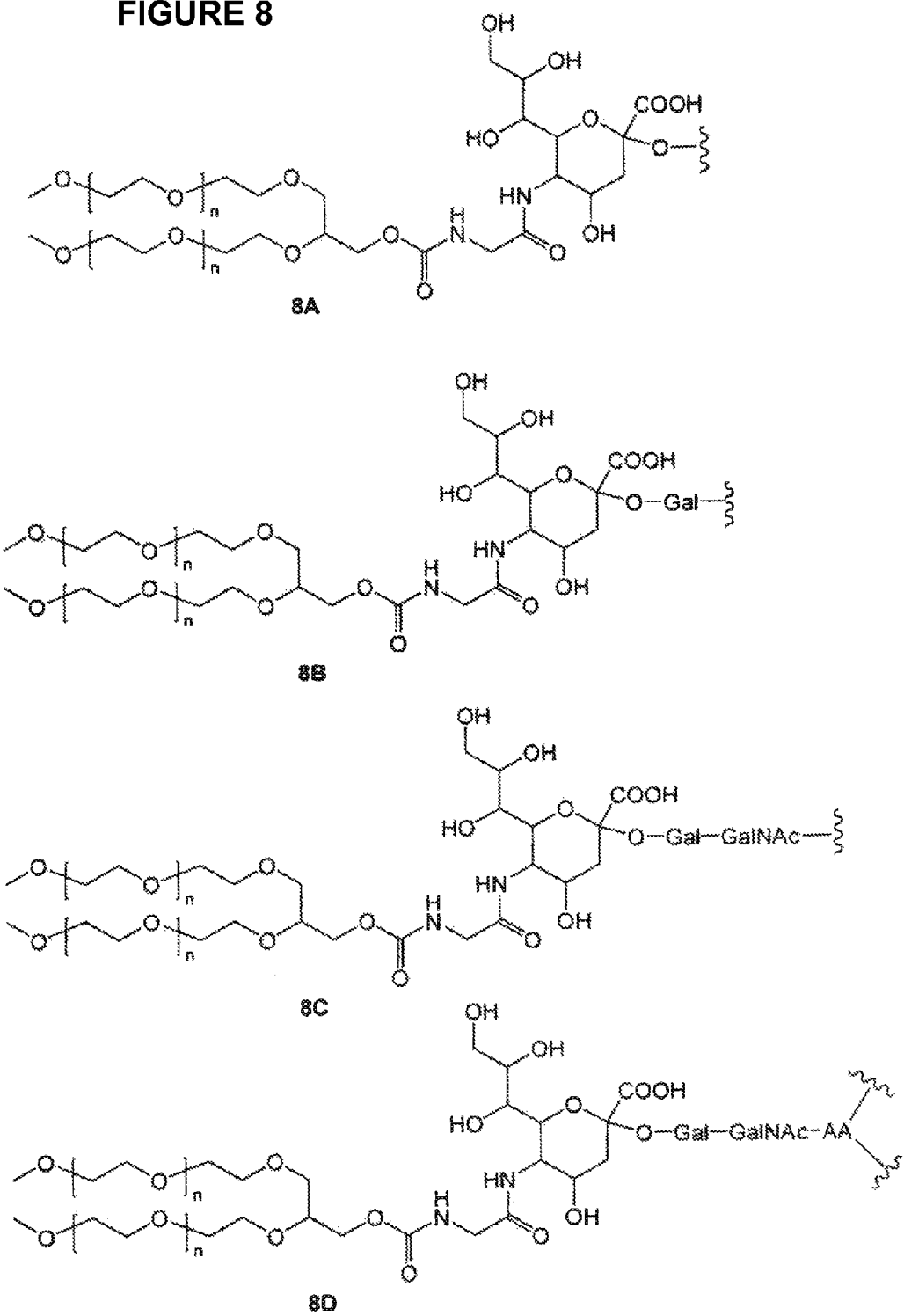
FIG. 8.

FIG. 4 shows clotting activity of O-glycoPEGylated rFVIII using various aPTT reagents. Data are shown as the ratio between the clotting activity and the chromogenic activity (A) or as the specific clotting activity (B). Mean and standard deviations of values from three independent experiments are shown.

TABLE 3

Rate of rFVIII activation and kinetic constants of FX activation by FIXa

| FVIII molecule | Rate of FVIII activation $10^{-3} \times min^{-1}$ | $K_{1/2FIXa}$ nM | FX Activation $K_m$ nM | $k_{cat}$ $s^{-1}$ |
|---|---|---|---|---|
| rFVIII | 10.4 ± 1.9 | 0.88 ± 0.46 | 7.9 ± 1.7 | 4.5 ± 1.9 |
| 40K-PEG-[O]-rFVIII | 9.9 ± 3.8 | 0.42 ± 0.02 | 6.4 ± 0.8 | 4.7 ± 0.2 |
| 80K-PEG-[O]-rFVIII | 9.8 ± 3.4 | 1.11 ± 0.12 | 8.2 ± 0.6 | 3.7 ± 0.4 |

Data are mean and standard deviations of 3-6 measurements.

Example 6

Pharmacokinetics of glycoPEGylated B-Domain Deleted (BDD)-FVIII in FVIII KO Mice and vWF KO Mice The pharmacokinetics of BDD-FVIII glycoPEGylated with various PEG sizes was studied following i.v. administration of 280 IU/kg to FVIII KO mice.

The following compounds were studied: BDD-FVIII, BDD-FVIII-10K PEG (O-glycan, 0129-0000-1005), BDD-FVIII-40K PEG (O-glycan, 0129-0000-1003), BDD-FVIII-2×40K PEG (O and N-glycan 0129-0000-1008-1A), BDD-FVIII-80K PEG (N-glycan, 0129-0000-1012, O-glycan 0129-0000-1009).

Design of Animal Studies:

Factor VIII knock out (FVIII KO) mice were bred at Taconic M&B, based on exon 16 KO in C57B1/6 background. A mixture of male and female (app.1:1) with an approximate weight of 25 g and age range of 19-26 weeks were employed. The mice were not fully back-crossed. No FVIII is detected in this mouse strain.

The mice were given single i.v. injections of 280 IU/kg in the tail vein with the compounds listed above. If a mouse was dosed peri-veneously, the mouse was exchanged with another mouse. After dosing, orbital plexus blood samples were collected from pre-dose until 64 hours after dosing using non-coated capillary glass tubes. Three samples were taken from each mouse, and 2, 3 or 4 samples were collected at each time point. Blood was stabilised in sodium citrate (9:1) and diluted in FVIII COA SP buffer (1:4) before centrifugation for 5 minutes at 4000 g. Plasma obtained from diluted blood was frozen at dry ice at kept at −80° C. before quantitative analysis by means of FVIII chromogenic activity and/or FVIII antigen analysis.

Quantitative Plasma Analysis:

The FVIII chromogenic activity was determined by the use of reagents from the Coatest SP kit (Chromogenix). Diluted plasma samples, calibrators (ILS calibration plasma) in Coatest SP-buffer, and buffer negative control (50 μl) were added to 96-well microtiter plates (Nunc) in duplicates. The Factor IXa/Factor X reagent, the phospholipid reagent and $CaCl_2$ from the Coatest SP kit were mixed 5:1:3 (vol:vol:vol) and 75 μl of this added to the wells. After 15 min incubation at room temperature 50 μl of the Factor Xa substrate S-2765/thrombin inhibitor I-2581 mix was added and the reactions incubated 10 min at room temperature before 25 μl 2% citric acid was added. The absorbance at 405 nm was measured on a Spectramax microtiter plate reader (Molecular Devices). FVIII activity in the plasma samples was calculated from the calibration curve made by dilutions of the calibrated international plasma standard (ILS).

The FVIII antigen assay was a commercial available ELISA kit from Diagnostica Stago (Asserachrom VIII:CAg) using two monoclonal antibodies directed against the light chain of human FVIII. Calibrators (dilutions of the compounds) or plasma samples were diluted at least 50-fold in coatest SP dilution buffer supplied by the kit were applied to the precoated wells and the ELISA performed according to the manufactures instructions. The values used for reporting the pharmacokinetic study are based on the standard curve made from the compounds themselves.

Pharmacokinetic Parameters Estimations:

Pharmacokinetic analysis was carried out by non-compartmental methods (NCA) of data using ILS as calibrator (data based on chromogenic activity), using the compounds themselves as calibrator (data based on ELISA). From the data the following parameters were estimated: Cmax (maximum concentration, after i.v. administration this is at the first sampling time point), Tmax (time of maximum concentration, after i.v. administration this is the first time point), AUCO-∞ (area under the curve from time 0 to infinity), T1/2, (terminal half-live), CL (clearance) and Vss (volume of distribution at steady state). All calculations were performed using WinNonlin Pro version 4.1.

After i.v. injection of 280 IU/Kg BDD-FVIII, BDD-FVIII-10 KDa PEG, BDD-FVIII-40 KDa PEG, BDD-FVIII-2×40 KDa PEG and BDD-FVIII-80 KDa PEG to FVIII KO mice, the half-life increased along with increasing PEG size in the range of 7.8 h (BDD-FVIII) to 15-16 h (Table 4), which corresponds to a 2-fold increase. Similarly, the clearance was reduced and the MRT increased with increasing PEG sizes (Table 4).

TABLE 4

Pharmacokinetic parameters estimates of FVIII glycoPEGylated with different sizes of PEG after i.v. administration to FVIII KO mice based on chromogenic activity (BDD: B-domain deleted).

| Compound | Dose (IU/kg) | T½ (h) | CL (ml/h/kg) | MRT (h) | Prolongation (fold) |
|---|---|---|---|---|---|
| BDD-FVIII | 280 | 6.7-9.3 | 8.1-10 | 9.9-11 | 1 |
| BDD-FVIII 10 KDa PEG (O-glycan) | 280 | 10 | 8.5 | 16 | 1.3 |
| BDD-FVIII-2 × 40 KDa PEG | 280 | 13 | 5.8 | 19 | 1.9-2.1 |
| BDD-FVIII 40 KDa PEG (O-glycan) | 280 | 15-16 | 3.6-3.8 | 20-22 | 1.7 |
| BDD-FVIII 80 KDa PEG (O-glycan) | 280 | 15 | 6.4 | 21 | 1.9 |

Conclusion:

GlycoPEGylation of BDD-FVIII increased the T1/2 1.3-2.1 fold as compared to BDD-FVIII after i.v. administration of 280 IU/kg to FVIII KO mice. An increasing T1/2 was observed as the size of the PEG group was increased in the range of 10 KDa to 80 KDa PEG.

Example 7

Prolonged Haemostatic Effect of 40K-PEG-[O]-N8 Compared to Advate in a FeCl3 Induced Injury Model in Haemophilia a Mice The duration of action of 40K-PEG-[O]-N8 vs. recombinant FVIII (Advate) was investigated in a FeCl3 induced injury model in haemophilia A (F8-KO) mice.

Mice were anesthetized and placed on a heating pad (37° C.) to maintain body temperature. The carotid artery was exposed and a flow-probe (0.5PSB Nanoprobe) that measures blood flow by ultrasound was placed around the artery. The injury (an iron-mediated chemical oxidation) was induced by applying a filter paper (2×5 mm) briefly soaked in a 10% FeCl3 solution around the exposed carotid artery. The filter paper was removed after 3 min. The artery was then washed three times with 0.9% NaCl and finally Surgilube (an acoustic coupler) was applied in order to displace air in the flow-probe and secure an optimised measurement of the blood flow. Blood flow (ml/min) was recorded for 25 min after removing the FeCl3 saturated filter paper and the time to occlusion was determined by measuring the time (in min) from removal of FeCl3 saturated filter paper until the blood flow was 0 ml/min. If occlusion did not occur after 25 min the occlusion time was reported as 25 min even though no occlusion occurred during the observation period. F8-KO mice (n=6-10) were treated with Advate (280 U/kg), 40K-PEG-[O]-N8 (280 U/kg), or vehicle. The FeCl3 induced injury was made 5 min (acute effect) or 24, 48, 60, and 72 hours after dosing. The blood flow (ml/min) was recorded for 25 min after removal of FeCl3, and subsequently the time to occlusion was determined.

No occlusion occurred in vehicle treated F8-KO mice, whereas occlusion occurred in all mice treated with 40 KDa-PEG-[O]-N8 and Advate 5 min after dosing (acute effect) with a mean occlusion time of 4.3±0.4 min and 5.2±0.7 min, respectively. In 40 KDa-PEG-[O]-N8 treated F8-KO mice the average occlusion time increased to 13.8±3.4 min at 72 hours after dosing. In contrast the Advate treated F8-KO mice had an occlusion time of 13.0±3.4 min and 15.9±2.9 min after 24 and 48 hours, respectively. Importantly no occlusions were observed 60 and 72 hours after administration of Advate. In all mice treated with 40 KDa-PEG-[O]-N8 occlusion was observed 24 hours after dosing whereas only 67% of the mice treated with Advate occluded. After 72 hours occlusion was still seen in 63% of the mice treated with 40 KDa-PEG-[O]-N8, whereas no occlusion was observed 60 and 72 hours after administration of Advate.

Prolonged Effect of 40 KDa-PEG-[O]-N8 in F8-KO Mice.

The FeCl3 induced injury was made 5 min (acute effect), 24, 48, 60, and 72 hours after dosing 280 IU/kg 40 KDa-PEG-[O]-N8, 280 IU/kg Advate, or vehicle. The blood flow (mL/min) was recorded for 25 min after removal of FeCl3, and subsequently the time to occlusion was determined. At 60 and 72 hours after dosing no occlusion occurred in mice dosed with Advate. Mean and SEM of 6-10 mice per group are shown. Time to occlusion between the different groups was compared using Kruskal-Wallis test including Dunn's post test. *: p<0.05; **: p<0.01.

In conclusion, the haemostatic effect of 40 KDa-PEG-[O]-N8 is significantly prolonged compared to Advate in a FeCl3 induced injury model in F8-KO mice.

What is claimed:

1. A Factor VIII molecule with a modified circulatory half life comprising a FVIII molecule with a truncated B-domain consisting of amino acids 741-760 of SEQ ID NO: 2, wherein the FVIII molecule is covalently conjugated to a PEG via an O-linked oligosaccharide on a serine residue corresponding to position 750 of SEQ ID NO: 2, wherein the size of the PEG is about 40,000 Da.

2. The FVIII molecule of claim 1 made by a process comprising:
   a) transfecting a mammalian host cell with a vector encoding the FVIII molecule of claim 1;
   b) culturing the host cell of step (a) under conditions suitable to express the FVIII molecule in the host cell;
   c) harvesting the FVIII molecule from the host cell culture of step (b); and
   d) covalently conjugating the FVIII molecule with the PEG via an O-linked oligosaccharide on the serine residue corresponding to position 750 of SEQ ID NO: 2, wherein the size of the PEG is about 40,000 Da.

3. The FVIII molecule of claim 2, wherein the mammalian host cell is a CHO cell.

4. A pharmaceutical composition comprising the FVIII molecule of claim 1.

5. A pharmaceutical composition comprising the FVIII molecule of claim 2.

6. A method of treating a haemophilic disease comprising administering to a patient in need thereof a therapeutically effective amount of the pharmaceutical composition of claim 4.

7. A method of treating a haemophilic disease comprising administering to a patient in need thereof a therapeutically effective amount of the pharmaceutical composition of claim 5.

* * * * *

SEQUENCE LISTING

```
<160> NUMBER OF SEQ ID NOS: 3

<210> SEQ ID NO 1
<211> LENGTH: 2332
<212> TYPE: PRT
<213> ORGANISM: Homo sapiens

<400> SEQUENCE: 1

Ala Thr Arg Arg Tyr Tyr Leu Gly Ala Val Glu Leu Ser Trp Asp Tyr
1               5                   10                  15
```

```
Met Gln Ser Asp Leu Gly Glu Leu Pro Val Asp Ala Arg Phe Pro Pro
             20                  25                  30
Arg Val Pro Lys Ser Phe Pro Phe Asn Thr Ser Val Tyr Lys Lys
         35                  40                  45
Thr Leu Phe Val Glu Phe Thr Asp His Leu Phe Asn Ile Ala Lys Pro
 50                  55                  60
Arg Pro Pro Trp Met Gly Leu Leu Gly Pro Thr Ile Gln Ala Glu Val
 65                  70                  75                  80
Tyr Asp Thr Val Val Ile Thr Leu Lys Asn Met Ala Ser His Pro Val
                 85                  90                  95
Ser Leu His Ala Val Gly Val Ser Tyr Trp Lys Ala Ser Glu Gly Ala
                100                 105                 110
Glu Tyr Asp Asp Gln Thr Ser Gln Arg Glu Lys Glu Asp Asp Lys Val
             115                 120                 125
Phe Pro Gly Gly Ser His Thr Tyr Val Trp Gln Val Leu Lys Glu Asn
             130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
             180                 185                 190
His Lys Phe Ile Leu Leu Phe Ala Val Phe Asp Glu Gly Lys Ser Trp
         195                 200                 205
His Ser Glu Thr Lys Asn Ser Leu Met Gln Asp Arg Asp Ala Ala Ser
 210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
             260                 265                 270
Gly His Thr Phe Leu Val Arg Asn His Arg Gln Ala Ser Leu Glu Ile
         275                 280                 285
Ser Pro Ile Thr Phe Leu Thr Ala Gln Thr Leu Leu Met Asp Leu Gly
 290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
             340                 345                 350
Ser Glu Met Asp Val Val Arg Phe Asp Asp Asp Asn Ser Pro Ser Phe
         355                 360                 365
Ile Gln Ile Arg Ser Val Ala Lys Lys His Pro Lys Thr Trp Val His
 370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
             420                 425                 430
Asp Glu Thr Phe Lys Thr Arg Glu Ala Ile Gln His Glu Ser Gly Ile
         435                 440                 445
```

```
Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
```

```
                865                 870                 875                 880
Thr Ser Asn Asn Leu Ile Ser Thr Ile Pro Ser Asp Asn Leu Ala Ala
                885                 890                 895
Gly Thr Asp Asn Thr Ser Ser Leu Gly Pro Pro Ser Met Pro Val His
                900                 905                 910
Tyr Asp Ser Gln Leu Asp Thr Thr Leu Phe Gly Lys Lys Ser Ser Pro
                915                 920                 925
Leu Thr Glu Ser Gly Gly Pro Leu Ser Leu Ser Glu Glu Asn Asn Asp
                930                 935                 940
Ser Lys Leu Leu Glu Ser Gly Leu Met Asn Ser Gln Glu Ser Ser Trp
945                 950                 955                 960
Gly Lys Asn Val Ser Ser Thr Glu Ser Gly Arg Leu Phe Lys Gly Lys
                965                 970                 975
Arg Ala His Gly Pro Ala Leu Leu Thr Lys Asp Asn Ala Leu Phe Lys
                980                 985                 990
Val Ser Ile Ser Leu Leu Lys Thr Asn Lys Thr Ser Asn Asn Ser Ala
                995                1000                1005
Thr Asn Arg Lys Thr His Ile Asp Gly Pro Ser Leu Leu Ile Glu
    1010                1015                1020
Asn Ser Pro Ser Val Trp Gln Asn Ile Leu Glu Ser Asp Thr Glu
    1025                1030                1035
Phe Lys Lys Val Thr Pro Leu Ile His Asp Arg Met Leu Met Asp
    1040                1045                1050
Lys Asn Ala Thr Ala Leu Arg Leu Asn His Met Ser Asn Lys Thr
    1055                1060                1065
Thr Ser Ser Lys Asn Met Glu Met Val Gln Gln Lys Lys Glu Gly
    1070                1075                1080
Pro Ile Pro Pro Asp Ala Gln Asn Pro Asp Met Ser Phe Phe Lys
    1085                1090                1095
Met Leu Phe Leu Pro Glu Ser Ala Arg Trp Ile Gln Arg Thr His
    1100                1105                1110
Gly Lys Asn Ser Leu Asn Ser Gly Gln Gly Pro Ser Pro Lys Gln
    1115                1120                1125
Leu Val Ser Leu Gly Pro Glu Lys Ser Val Glu Gly Gln Asn Phe
    1130                1135                1140
Leu Ser Glu Lys Asn Lys Val Val Val Gly Lys Gly Glu Phe Thr
    1145                1150                1155
Lys Asp Val Gly Leu Lys Glu Met Val Phe Pro Ser Ser Arg Asn
    1160                1165                1170
Leu Phe Leu Thr Asn Leu Asp Asn Leu His Glu Asn Asn Thr His
    1175                1180                1185
Asn Gln Glu Lys Lys Ile Gln Glu Glu Ile Glu Lys Lys Glu Thr
    1190                1195                1200
Leu Ile Gln Glu Asn Val Val Leu Pro Gln Ile His Thr Val Thr
    1205                1210                1215
Gly Thr Lys Asn Phe Met Lys Asn Leu Phe Leu Leu Ser Thr Arg
    1220                1225                1230
Gln Asn Val Glu Gly Ser Tyr Asp Gly Ala Tyr Ala Pro Val Leu
    1235                1240                1245
Gln Asp Phe Arg Ser Leu Asn Asp Ser Thr Asn Arg Thr Lys Lys
    1250                1255                1260
His Thr Ala His Phe Ser Lys Lys Gly Glu Glu Glu Asn Leu Glu
    1265                1270                1275
```

```
Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305

Gln Arg Ser Lys Arg Ala Leu Lys Gln Phe Arg Leu Pro Leu Glu
    1310                1315                1320

Glu Thr Glu Leu Glu Lys Arg Ile Ile Val Asp Asp Thr Ser Thr
    1325                1330                1335

Gln Trp Ser Lys Asn Met Lys His Leu Thr Pro Ser Thr Leu Thr
    1340                1345                1350

Gln Ile Asp Tyr Asn Glu Lys Glu Lys Gly Ala Ile Thr Gln Ser
    1355                1360                1365

Pro Leu Ser Asp Cys Leu Thr Arg Ser His Ser Ile Pro Gln Ala
    1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
    1400                1405                1410

Ser His Leu Pro Ala Ala Ser Tyr Arg Lys Lys Asp Ser Gly Val
    1415                1420                1425

Gln Glu Ser Ser His Phe Leu Gln Gly Ala Lys Lys Asn Asn Leu
    1430                1435                1440

Ser Leu Ala Ile Leu Thr Leu Glu Met Thr Gly Asp Gln Arg Glu
    1445                1450                1455

Val Gly Ser Leu Gly Thr Ser Ala Thr Asn Ser Val Thr Tyr Lys
    1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
    1490                1495                1500

Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680
```

```
Glu Asn Gln Ser Pro Arg Ser Phe Gln Lys Lys Thr Arg His Tyr
    1685            1690                1695

Phe Ile Ala Ala Val Glu Arg Leu Trp Asp Tyr Gly Met Ser Ser
    1700            1705                1710

Ser Pro His Val Leu Arg Asn Arg Ala Gln Ser Gly Ser Val Pro
    1715            1720                1725

Gln Phe Lys Lys Val Val Phe Gln Glu Phe Thr Asp Gly Ser Phe
    1730            1735                1740

Thr Gln Pro Leu Tyr Arg Gly Glu Leu Asn Glu His Leu Gly Leu
    1745            1750                1755

Leu Gly Pro Tyr Ile Arg Ala Glu Val Glu Asp Asn Ile Met Val
    1760            1765                1770

Thr Phe Arg Asn Gln Ala Ser Arg Pro Tyr Ser Phe Tyr Ser Ser
    1775            1780                1785

Leu Ile Ser Tyr Glu Glu Asp Gln Arg Gln Gly Ala Glu Pro Arg
    1790            1795                1800

Lys Asn Phe Val Lys Pro Asn Glu Thr Lys Thr Tyr Phe Trp Lys
    1805            1810                1815

Val Gln His His Met Ala Pro Thr Lys Asp Glu Phe Asp Cys Lys
    1820            1825                1830

Ala Trp Ala Tyr Phe Ser Asp Val Asp Leu Glu Lys Asp Val His
    1835            1840                1845

Ser Gly Leu Ile Gly Pro Leu Leu Val Cys His Thr Asn Thr Leu
    1850            1855                1860

Asn Pro Ala His Gly Arg Gln Val Thr Val Gln Glu Phe Ala Leu
    1865            1870                1875

Phe Phe Thr Ile Phe Asp Glu Thr Lys Ser Trp Tyr Phe Thr Glu
    1880            1885                1890

Asn Met Glu Arg Asn Cys Arg Ala Pro Cys Asn Ile Gln Met Glu
    1895            1900                1905

Asp Pro Thr Phe Lys Glu Asn Tyr Arg Phe His Ala Ile Asn Gly
    1910            1915                1920

Tyr Ile Met Asp Thr Leu Pro Gly Leu Val Met Ala Gln Asp Gln
    1925            1930                1935

Arg Ile Arg Trp Tyr Leu Leu Ser Met Gly Ser Asn Glu Asn Ile
    1940            1945                1950

His Ser Ile His Phe Ser Gly His Val Phe Thr Val Arg Lys Lys
    1955            1960                1965

Glu Glu Tyr Lys Met Ala Leu Tyr Asn Leu Tyr Pro Gly Val Phe
    1970            1975                1980

Glu Thr Val Glu Met Leu Pro Ser Lys Ala Gly Ile Trp Arg Val
    1985            1990                1995

Glu Cys Leu Ile Gly Glu His Leu His Ala Gly Met Ser Thr Leu
    2000            2005                2010

Phe Leu Val Tyr Ser Asn Lys Cys Gln Thr Pro Leu Gly Met Ala
    2015            2020                2025

Ser Gly His Ile Arg Asp Phe Gln Ile Thr Ala Ser Gly Gln Tyr
    2030            2035                2040

Gly Gln Trp Ala Pro Lys Leu Ala Arg Leu His Tyr Ser Gly Ser
    2045            2050                2055

Ile Asn Ala Trp Ser Thr Lys Glu Pro Phe Ser Trp Ile Lys Val
    2060            2065                2070

Asp Leu Leu Ala Pro Met Ile Ile His Gly Ile Lys Thr Gln Gly
```

```
                    2075                2080                2085

Ala Arg Gln Lys Phe Ser Ser Leu Tyr Ile Ser Gln Phe Ile Ile
        2090                2095                2100

Met Tyr Ser Leu Asp Gly Lys Lys Trp Gln Thr Tyr Arg Gly Asn
        2105                2110                2115

Ser Thr Gly Thr Leu Met Val Phe Phe Gly Asn Val Asp Ser Ser
        2120                2125                2130

Gly Ile Lys His Asn Ile Phe Asn Pro Pro Ile Ile Ala Arg Tyr
        2135                2140                2145

Ile Arg Leu His Pro Thr His Tyr Ser Ile Arg Ser Thr Leu Arg
        2150                2155                2160

Met Glu Leu Met Gly Cys Asp Leu Asn Ser Cys Ser Met Pro Leu
        2165                2170                2175

Gly Met Glu Ser Lys Ala Ile Ser Asp Ala Gln Ile Thr Ala Ser
        2180                2185                2190

Ser Tyr Phe Thr Asn Met Phe Ala Thr Trp Ser Pro Ser Lys Ala
        2195                2200                2205

Arg Leu His Leu Gln Gly Arg Ser Asn Ala Trp Arg Pro Gln Val
        2210                2215                2220

Asn Asn Pro Lys Glu Trp Leu Gln Val Asp Phe Gln Lys Thr Met
        2225                2230                2235

Lys Val Thr Gly Val Thr Thr Gln Gly Val Lys Ser Leu Leu Thr
        2240                2245                2250

Ser Met Tyr Val Lys Glu Phe Leu Ile Ser Ser Ser Gln Asp Gly
        2255                2260                2265

His Gln Trp Thr Leu Phe Phe Gln Asn Gly Lys Val Lys Val Phe
        2270                2275                2280

Gln Gly Asn Gln Asp Ser Phe Thr Pro Val Val Asn Ser Leu Asp
        2285                2290                2295

Pro Pro Leu Leu Thr Arg Tyr Leu Arg Ile His Pro Gln Ser Trp
        2300                2305                2310

Val His Gln Ile Ala Leu Arg Met Glu Val Leu Gly Cys Glu Ala
        2315                2320                2325

Gln Asp Leu Tyr
        2330

<210> SEQ ID NO 2
<211> LENGTH: 1445
<212> TYPE: PRT
<213> ORGANISM: Artificial Sequence
<220> FEATURE:
<223> OTHER INFORMATION: B-domain truncated human Factor VIII

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95
```

```
Ser Leu His Ala Val Gly Val Ser Tyr Trp Lys Ala Ser Glu Gly Ala
            100                 105                 110
Glu Tyr Asp Asp Gln Thr Ser Gln Arg Glu Lys Glu Asp Asp Lys Val
            115                 120                 125
Phe Pro Gly Gly Ser His Thr Tyr Val Trp Gln Val Leu Lys Glu Asn
130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
                180                 185                 190
His Lys Phe Ile Leu Leu Phe Ala Val Phe Asp Glu Gly Lys Ser Trp
                195                 200                 205
His Ser Glu Thr Lys Asn Ser Leu Met Gln Asp Arg Asp Ala Ala Ser
            210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
                260                 265                 270
Gly His Thr Phe Leu Val Arg Asn His Arg Gln Ala Ser Leu Glu Ile
                275                 280                 285
Ser Pro Ile Thr Phe Leu Thr Ala Gln Thr Leu Leu Met Asp Leu Gly
            290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
                340                 345                 350
Ser Glu Met Asp Val Val Arg Phe Asp Asp Asp Asn Ser Pro Ser Phe
            355                 360                 365
Ile Gln Ile Arg Ser Val Ala Lys Lys His Pro Lys Thr Trp Val His
            370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
```

-continued

```
              515                 520                 525
Leu Thr Arg Tyr Tyr Ser Ser Phe Val Asn Met Glu Arg Asp Leu Ala
530                 535                 540

Ser Gly Leu Ile Gly Pro Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Gln Asn
                740                 745                 750

Pro Pro Val Leu Lys Arg His Gln Arg Glu Ile Thr Arg Thr Thr Leu
            755                 760                 765

Gln Ser Asp Gln Glu Glu Ile Asp Tyr Asp Asp Thr Ile Ser Val Glu
770                 775                 780

Met Lys Lys Glu Asp Phe Asp Ile Tyr Asp Glu Asp Glu Asn Gln Ser
785                 790                 795                 800

Pro Arg Ser Phe Gln Lys Lys Thr Arg His Tyr Phe Ile Ala Ala Val
                805                 810                 815

Glu Arg Leu Trp Asp Tyr Gly Met Ser Ser Ser Pro His Val Leu Arg
                820                 825                 830

Asn Arg Ala Gln Ser Gly Ser Val Pro Gln Phe Lys Lys Val Val Phe
            835                 840                 845

Gln Glu Phe Thr Asp Gly Ser Phe Thr Gln Pro Leu Tyr Arg Gly Glu
850                 855                 860

Leu Asn Glu His Leu Gly Leu Leu Gly Pro Tyr Ile Arg Ala Glu Val
865                 870                 875                 880

Glu Asp Asn Ile Met Val Thr Phe Arg Asn Gln Ala Ser Arg Pro Tyr
                885                 890                 895

Ser Phe Tyr Ser Ser Leu Ile Ser Tyr Glu Glu Asp Gln Arg Gln Gly
                900                 905                 910

Ala Glu Pro Arg Lys Asn Phe Val Lys Pro Asn Glu Thr Lys Thr Tyr
            915                 920                 925

Phe Trp Lys Val Gln His His Met Ala Pro Thr Lys Asp Glu Phe Asp
930                 935                 940
```

-continued

Cys Lys Ala Trp Ala Tyr Phe Ser Asp Val Asp Leu Glu Lys Asp Val
945                 950                 955                 960

His Ser Gly Leu Ile Gly Pro Leu Leu Val Cys His Thr Asn Thr Leu
        965                 970                 975

Asn Pro Ala His Gly Arg Gln Val Thr Val Gln Glu Phe Ala Leu Phe
            980                 985                 990

Phe Thr Ile Phe Asp Glu Thr Lys Ser Trp Tyr Phe Thr Glu Asn Met
        995                 1000                1005

Glu Arg Asn Cys Arg Ala Pro Cys Asn Ile Gln Met Glu Asp Pro
    1010                1015                1020

Thr Phe Lys Glu Asn Tyr Arg Phe His Ala Ile Asn Gly Tyr Ile
    1025                1030                1035

Met Asp Thr Leu Pro Gly Leu Val Met Ala Gln Asp Gln Arg Ile
    1040                1045                1050

Arg Trp Tyr Leu Leu Ser Met Gly Ser Asn Glu Asn Ile His Ser
    1055                1060                1065

Ile His Phe Ser Gly His Val Phe Thr Val Arg Lys Lys Glu Glu
    1070                1075                1080

Tyr Lys Met Ala Leu Tyr Asn Leu Tyr Pro Gly Val Phe Glu Thr
    1085                1090                1095

Val Glu Met Leu Pro Ser Lys Ala Gly Ile Trp Arg Val Glu Cys
    1100                1105                1110

Leu Ile Gly Glu His Leu His Ala Gly Met Ser Thr Leu Phe Leu
    1115                1120                1125

Val Tyr Ser Asn Lys Cys Gln Thr Pro Leu Gly Met Ala Ser Gly
    1130                1135                1140

His Ile Arg Asp Phe Gln Ile Thr Ala Ser Gly Gln Tyr Gly Gln
    1145                1150                1155

Trp Ala Pro Lys Leu Ala Arg Leu His Tyr Ser Gly Ser Ile Asn
    1160                1165                1170

Ala Trp Ser Thr Lys Glu Pro Phe Ser Trp Ile Lys Val Asp Leu
    1175                1180                1185

Leu Ala Pro Met Ile Ile His Gly Ile Lys Thr Gln Gly Ala Arg
    1190                1195                1200

Gln Lys Phe Ser Ser Leu Tyr Ile Ser Gln Phe Ile Ile Met Tyr
    1205                1210                1215

Ser Leu Asp Gly Lys Lys Trp Gln Thr Tyr Arg Gly Asn Ser Thr
    1220                1225                1230

Gly Thr Leu Met Val Phe Phe Gly Asn Val Asp Ser Ser Gly Ile
    1235                1240                1245

Lys His Asn Ile Phe Asn Pro Pro Ile Ile Ala Arg Tyr Ile Arg
    1250                1255                1260

Leu His Pro Thr His Tyr Ser Ile Arg Ser Thr Leu Arg Met Glu
    1265                1270                1275

Leu Met Gly Cys Asp Leu Asn Ser Cys Ser Met Pro Leu Gly Met
    1280                1285                1290

Glu Ser Lys Ala Ile Ser Asp Ala Gln Ile Thr Ala Ser Ser Tyr
    1295                1300                1305

Phe Thr Asn Met Phe Ala Thr Trp Ser Pro Ser Lys Ala Arg Leu
    1310                1315                1320

His Leu Gln Gly Arg Ser Asn Ala Trp Arg Pro Gln Val Asn Asn
    1325                1330                1335

Pro Lys Glu Trp Leu Gln Val Asp Phe Gln Lys Thr Met Lys Val
    1340                1345                1350

```
Thr Gly Val Thr Thr Gln Gly Val Lys Ser Leu Leu Thr Ser Met
    1355            1360            1365

Tyr Val Lys Glu Phe Leu Ile Ser Ser Ser Gln Asp Gly His Gln
    1370            1375            1380

Trp Thr Leu Phe Phe Gln Asn Gly Lys Val Lys Val Phe Gln Gly
    1385            1390            1395

Asn Gln Asp Ser Phe Thr Pro Val Val Asn Ser Leu Asp Pro Pro
    1400            1405            1410

Leu Leu Thr Arg Tyr Leu Arg Ile His Pro Gln Ser Trp Val His
    1415            1420            1425

Gln Ile Ala Leu Arg Met Glu Val Leu Gly Cys Glu Ala Gln Asp
    1430            1435            1440

Leu Tyr
    1445

<210> SEQ ID NO 3
<211> LENGTH: 21
<212> TYPE: PRT
<213> ORGANISM: Artificial Sequence
<220> FEATURE:
<223> OTHER INFORMATION: Truncated B-domain of human factor VIII

<400> SEQUENCE: 3

Ser Phe Ser Gln Asn Ser Arg His Pro Ser Gln Asn Pro Pro Val Leu
1               5                   10                  15

Lys Arg His Gln Arg
            20
```